United States Patent
Klun et al.

(10) Patent No.: US 8,015,970 B2
(45) Date of Patent: *Sep. 13, 2011

(54) RESPIRATOR, WELDING HELMET, OR FACE SHIELD THAT HAS LOW SURFACE ENERGY HARD-COAT LENS

(75) Inventors: Thomas P. Klun, Lakeland, MN (US); Zai-Ming Qiu, Woodbury, MN (US); Gerald R. Hofmann, Oakdale, MN (US); Andrew S. Viner, Roseville, MN (US); Oscar S. Benz, Minneapolis, MN (US); Suresh Iyer, Woodbury, MN (US); Gregory D. Clark, St. Paul, MN (US); Craig A. Burton, Woodbury, MN (US); Mark J. Pellerite, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1060 days.

This patent is subject to a terminal disclaimer.

(21) Appl. No.: 11/828,566

(22) Filed: Jul. 26, 2007

(65) Prior Publication Data

US 2009/0025727 A1    Jan. 29, 2009

(51) Int. Cl.
*A62B 18/02*    (2006.01)

(52) U.S. Cl. .............. 128/201.21; 128/201.24

(58) Field of Classification Search ............ 128/201.22, 128/201.23, 201.24, 201.27, 201.21; 428/422, 428/423.1
See application file for complete search history.

(56) References Cited

U.S. PATENT DOCUMENTS

| | | | |
|---|---|---|---|
| 3,868,727 A | 3/1975 | Paschall |
| 3,986,997 A | 10/1976 | Clark |
| 4,188,451 A | 2/1980 | Humphrey, Jr. |
| 4,262,072 A | 4/1981 | Wendling et al. |
| 4,378,250 A | 3/1983 | Treadway et al. |
| 4,624,870 A | 11/1986 | Anthonly |
| 4,707,860 A | 11/1987 | Holmstrom |
| 4,863,244 A | 9/1989 | Fuerthbauer et al. |
| 4,944,962 A | 7/1990 | Furuta et al. |

(Continued)

FOREIGN PATENT DOCUMENTS

DE    10004132 A1    8/2001

(Continued)

OTHER PUBLICATIONS

U.S. Appl. No. 11/683,823, filed Mar. 8, 2007, Iyer et al.

(Continued)

*Primary Examiner* — Thao T. Tran
(74) *Attorney, Agent, or Firm* — Karl G. Hanson

(57) ABSTRACT

A personal safety protective device that includes a lens and a support structure onto which the lens is secured. The lens includes a substrate and a hard-coat layer located on the substrate of the lens. The hard-coat layer has a low surface energy outer surface that is derived from a) an additive that includes at least one of i) a perfluoropolyether urethane that includes hydrolysable silane groups, and ii) an acrylate polymer that includes at least one perfluoropolyether moiety and at least one hydrolysable silane group, and b) a silsesquioxane-based hard-coat composition. The provision of such a lens on a personal safety protective device enables the lens to be durable to abrasion and to be easily cleaned without use of solvents that could shorten the service life of the lens.

21 Claims, 3 Drawing Sheets

U.S. PATENT DOCUMENTS

| | | | |
|---|---|---|---|
| 5,041,313 A | 8/1991 | Patel | |
| H1023 H | 3/1992 | Wiseman, Sr. | |
| 5,191,468 A | 3/1993 | Mases | |
| 5,274,159 A | 12/1993 | Pellerite et al. | |
| 5,303,423 A | 4/1994 | Gazzara et al. | |
| 5,303,701 A | 4/1994 | Heins et al. | |
| 5,411,807 A | 5/1995 | Patel et al. | |
| 5,446,925 A | 9/1995 | Baker et al. | |
| 5,498,445 A | 3/1996 | Steiner et al. | |
| 5,642,530 A | 7/1997 | Parks | |
| 5,825,441 A | 10/1998 | Hornell et al. | |
| 5,924,420 A | 7/1999 | Reischel et al. | |
| D416,649 S | 11/1999 | Burns et al. | |
| 6,055,666 A | 5/2000 | Eklund et al. | |
| 6,277,178 B1 | 8/2001 | Holmquist-Brown et al. | |
| 6,361,870 B1 | 3/2002 | Steffl et al. | |
| 6,518,357 B1 | 2/2003 | Rajagopalan et al. | |
| 6,582,823 B1 | 6/2003 | Sakhrani et al. | |
| 6,664,354 B2 | 12/2003 | Savu et al. | |
| 6,763,835 B1 | 7/2004 | Grove et al. | |
| 6,838,142 B2 | 1/2005 | Yang et al. | |
| 6,895,960 B2 | 5/2005 | Fabin | |
| 6,978,782 B2 | 12/2005 | Tayebi | |
| 7,094,829 B2 | 8/2006 | Audenaert et al. | |
| 7,097,910 B2 | 8/2006 | Moore et al. | |
| 7,147,671 B2 | 12/2006 | Butts et al. | |
| 7,166,329 B2 | 1/2007 | Dams | |
| 7,173,778 B2 | 2/2007 | Jing et al. | |
| 7,178,919 B2 | 2/2007 | Kato et al. | |
| 7,200,875 B2 | 4/2007 | Dondero | |
| 7,335,786 B1 | 2/2008 | Iyer et al. | |
| 7,652,116 B2 | 1/2010 | Clark et al. | |
| 2002/0109922 A1 | 8/2002 | Wilson et al. | |
| 2004/0077775 A1 | 4/2004 | Audenaert et al. | |
| 2004/0092675 A1 | 5/2004 | Moore et al. | |
| 2004/0147188 A1 | 7/2004 | Johnson et al. | |
| 2005/0002108 A1 | 1/2005 | Wilson et al. | |
| 2005/0054804 A1 | 3/2005 | Dams et al. | |
| 2005/0121644 A1 | 6/2005 | Dams et al. | |
| 2005/0143541 A1 | 6/2005 | Caldwell et al. | |
| 2005/0164010 A1 | 7/2005 | Trombetta | |
| 2006/0142519 A1 | 6/2006 | Qiu et al. | |
| 2007/0014018 A1* | 1/2007 | Wheatley et al. | 359/580 |
| 2007/0054133 A1 | 3/2007 | Sherman et al. | |
| 2007/0055019 A1 | 3/2007 | Sherman et al. | |

FOREIGN PATENT DOCUMENTS

| | | |
|---|---|---|
| EP | 1410775 A2 | 4/2004 |
| JP | 7117065 | 5/1995 |
| JP | 7316506 | 12/1995 |
| JP | 8318598 | 12/1996 |
| JP | 2005099381 | 4/2005 |
| JP | 2005331607 | 12/2005 |
| WO | 98/033079 A1 | 7/1998 |
| WO | 98/51724 | 11/1998 |
| WO | 01/17770 A1 | 3/2001 |
| WO | 2005/030891 | 4/2005 |
| WO | 2006/071567 | 7/2006 |
| WO | 2006/102383 | 9/2006 |

OTHER PUBLICATIONS

U.S. Appl. No. 60/871,034, filed Dec. 20, 2006, Iyer et al.

U.S. Appl. No. 60/870,300, filed Dec. 15, 2006, Clark.

Aearo Corporation, http://www.aosafety.com/industrial/face_detail.cfm?prod family=TuffMaster&ind_prod_num=82790-00000001, Mar. 20, 2007.

Scott Health & Safety, http://www.scotthealthsafety.com/lenscovers.htm, Nov. 19, 2003.

Momentive Performance Materials, http://www.gesilicones.com/siliconesweb/am1/en/documents/datasheets/303.html?SMSESSION=NO.

* cited by examiner

RESPIRATOR, WELDING HELMET, OR FACE SHIELD THAT HAS LOW SURFACE ENERGY HARD-COAT LENS

The present invention pertains to a full-face respirator, welding helmet, or face shield having a low surface energy hard-coat lens.

BACKGROUND

Lenses that are typically used in personal protection equipment—for example, full face piece respirators, welding helmets, and face shields—are commonly made from polycarbonate resins. These resins provide excellent visual clarity and demonstrate extraordinarily good impact resistance. Polycarbonate lenses, however, exhibit a particular drawback in that they can become easily scratched and may fracture when exposed to some common chemical solvents. Consequently, polycarbonate lenses are often coated with a protective silsesquioxane-based hard-coat composition, such as a methyltrimethoxysilane hydrolyzed in a mixture of water and alcoholic solvent and in the presence of a colloidal silica, an example of which is commercially available under the trade designation GE SHC 1200 from GE Silicones, (Waterford, N.Y.), to provide protection against both scratches and chemical crazing.

Another problem for workers who wear personal protection equipment, such as full face piece respirators, is that paint and other materials are splashed onto the lens, creating a staining pattern that can obstruct the wearer's vision. Common practice is to wipe the stain using a solvent-soaked rag. If the lens includes a protective hard-coat, the solvent may cause damage to the hard-coat, resulting in a shortened service life for the lens, or the solvent may wear away a portion or all of the hard-coat.

Hard-coat layers have been applied to a variety of substrates to increase the substrate's resistance to abrasion and degradation due to chemical exposure. However, known hard-coats have not addressed problems pertaining to stain resistance and cleanability.

SUMMARY OF THE INVENTION

The invention features a personal safety protective article that includes a lens that has a hard-coat layer located thereon, and a support structure to which the lens is secured. The hard-coat layer includes the reaction product of a) an additive that includes at least one of i) a perfluoropolyether urethane that includes hydrolysable silane groups and ii) an acrylate polymer that includes at least one perfluoropolyether moiety and at least one hydrolysable silane group, and b) a silsesquioxane-based hard coat composition. The hard-coat layer preferably exhibits low surface energy.

The inventors have discovered that the provision of a low surface energy outer-surface on the hard-coat layer of a lens can enable the lens to exhibit not only good scratch- and chemical-resistance but also good stain resistance and easy cleanability.

The invention features a coating that can exhibit improved scratch- and chemical-resistance, along with stain resistance and cleanability. The invention features a coating that can impart oil- and water-repellency properties, stain-release, stain-resistance characteristics, or a combination thereof, to a wide variety of substrates when formed as a layer on the substrate.

This invention accordingly relates to the use of optically clear, low-surface-energy, hard-coats that may impart improved stain resistance, scratch resistance, chemical resistance, and cleanability to lenses that are used in personal protection equipment.

The low surface energy coating inhibits and preferably prevents paint and sprayed compositions from adhering to and staining the lens. The low surface energy coating enables paint and sprayed compositions to bead up upon contact with the coating, rather than spread out and wet the surface. As a result, vision through the lens may remain unobstructed for longer periods of time relative to existing full-face respirators and welding helmets. The invention is also beneficial in that the contaminant can be readily removed by wiping, without the need for a solvent or other cleaning agent. Thus, lens cleaning is easier, and the life of the lens may be prolonged due to the decrease or elimination of the need to expose the lens to harsh cleaning agents.

GLOSSARY

The terms used in this document will be interpreted according to the following definitions:

"a", "an", and "the" include plural referents unless the content clearly indicates otherwise (thus, for example, reference to a composition containing "a compound" can include a mixture of two or more compounds);

"Alkyl" means a linear or branched, cyclic or acylic, saturated monovalent hydrocarbon radical, examples of which include methyl, ethyl, 1-propyl, 2-propyl, and pentyl;

"Acryloyl" means an acrylate, thioacrylate or acrylamide;

"Alkylene" means a linear saturated divalent hydrocarbon radical or a branched saturated divalent hydrocarbon radical, examples of which include methylene, ethylene, propylene, 2-methylpropylene, pentylene, and hexylene;

"Alkoxy" means an alkyl having a terminal oxygen atom, examples of which include $CH_3$—O— and $C_2H_5$—O—;

"Aralkylene" means an alkylene radical defined above with an aromatic group attached to the alkylene radical, examples of which include benzyl and 1-naphthylethyl.

"Cured" means dried (e.g., through the evaporation of water or organic solvent at ambient or elevated temperature), crosslinked or a combination thereof;

"Clean air" means a volume of atmospheric ambient air that has been filtered or otherwise processed to be essentially free of contaminants;

"Exterior gas space" means the ambient atmospheric gas space into which exhaled gas enters after passing through and beyond the mask body and/or exhalation valve or face shield;

"Face shield" means an article that includes a transparent lens that extends in front of a person's eyes, nose, and mouth and that protects a wearer's face in a workplace environment;

"Full face respirator" means a respirator that is worn over a person's nose, mouth, and eyes;

"Hard-coat layer" means a layer or coating that is located on the external surface of an object, which layer or coating has been designed to at least protect the object from abrasion;

"HFPO—" refers to the end group $F(CF(CF_3)CF_2O)_u CF(CF_3)$— of the methyl ester $F(CF(CF_3)CF_2O)UCF(CF_3)C(O)OCH_3$, wherein "u" averages from 1 to 50, which can be prepared according to the method disclosed in U.S. Pat. No. 3,250,808 (Moore et al.), with purification by fractional distillation, wherein the recitation of numerical ranges by endpoints includes all numbers subsumed within the range (e.g., the range 1 to 50 includes 1, 1.5, 3.33, and 50);

"Hydrolysable silane group" means a group that will undergo an exchange reaction with water to form a Si—OH moiety, which may further react to form siloxane groups.

Specific examples of hydrolysable groups include methoxy, ethoxy and propoxy groups, chlorine groups, and acetoxy groups;

"Interior gas space" means the space between the lens and a person's face;

"Lens" means a light-transmissible structure that is fashioned to be placed in front of a wearer's face and that allows the wearer to see the surrounding environment when looking through the structure;

"Monovalent perfluoropolyether moiety" refers to a perfluoropolyether chain that has one end terminated by a perfluoroalkyl group;

"Nucleophilic fluorine-containing compound" or "nucleophilic fluorinated compound" means a compound having at least one nucleophilic, isocyanate-reactive functional group (examples of which include a hydroxyl group and an amine group), and a perfluorooxyalkyl or perfluorooxyalkylene group, an example of which is $C_2F_5O(C_2F_4O)_3CF_2CONHC_2H_4OH$;

"or" is generally employed in its common sense and including "and/or" unless the content clearly dictates otherwise;

"Oxyalkoxy" has essentially the meaning given above for alkoxy except that at least one oxygen atom may be present in the alkyl chain, examples of which include $CH_3CH_2OCH_2CH_2O—$, $C_4H_9OCH_2CH_2OCH_2CH_2O—$, and $CH_3—O—(CH_2CH_2O)_{1-100}H$;

"Oxyalkyl" has essentially the meaning given above for alkyl except that at least one oxygen heteroatom may be present in the alkyl chain and heteroatoms are separated from each other by at least one carbon, examples of which include $CH_3CH_2OCH_2CH_2—$, $CH_3CH_2OCH_2CH_2OCH(CH_3)CH_2—$, and $C_4F_9CH_2OCH_2CH_2—$;

"Oxyalkylene" has essentially the meaning given above for alkylene except that at least one oxygen heteroatom may be present in the alkylene chain and heteroatoms are separated from each other by at least one carbon, examples of which include $—CH_2OCH_2O—$, $—CH_2CH_2OCH_2CH_2—$, and $—CH_2CH_2OCH_2CH_2CH_2—$;

"Perfluoroalkyl" has essentially the meaning given above for "alkyl" except that all or essentially all of the hydrogen atoms of the alkyl radical are replaced by fluorine atoms, examples of which include perfluoropropyl, perfluorobutyl, and perfluorooctyl;

"Perfluoroalkylene" has essentially the meaning given above for "alkylene" except that all or essentially all of the hydrogen atoms of the alkylene radical are replaced by fluorine atoms, examples of which include perfluoropropylene, perfluorobutylene, and perfluorooctylene;

"Perfluorooxyalkyl" has essentially the meaning given above for "oxyalkyl" except that all or essentially all of the hydrogen atoms of the oxyalkyl radical are replaced by fluorine atoms, examples of which include $CF_3CF_2OCF_2CF_2—$, $CF_3CF_2O(CF_2CF_2O)_3CF_2CF_2—$, and $C_3F_7O(CF(CF_3)CF_2O)_nCF(CF_3)CF_2—$, wherein s is from about 1 to about 50;

"Perfluorooxyalkylene" has essentially the meaning given above for "oxyalkylene" except that all or essentially all of the hydrogen atoms of the oxyalkylene radical are replaced by fluorine atoms, examples of which include $—CF_2OCF_2—$ and $—[CF_2—CF_2—O]_r—[CF(CF_3)—CF_2—O]_s—$, wherein r and s are integers of from 1 to 50;

"Perfluoroalkyleneoxy" has essentially the meaning given above for "Perfluorooxyalkylene," but requires that the group, as written from left to right, end in an oxygen atom;

"Perfluorinated group" means an organic group in which all or essentially all of the carbon bonded hydrogen atoms are replaced with fluorine atoms, examples of which include perfluoroalkyl and perfluorooxyalkyl;

"Pefluoropolyether urethane" refers to compounds of Formula 1 set forth below, and includes those compounds having urethane linkages per se, urea linkages, and/or thiourea linkages;

"Polyfunctional isocyanate" or "polyisocyanate compound" means a compound having an average of more than one isocyanate group, i.e., —NCO, attached to a multivalent organic group;

"Personal safety protective article" means a full-face respirator, a welding helmet, or a face shield;

"Plastic" means a material that includes polymers and optionally other ingredients;

"Respirator" means a device that is capable of supplying clean air to a wearer of the device;

"Silsesquioxane-based hard-coat composition" means a composition that includes condensates (i.e., hydrolysates) of alkoxysilanes formed in the presence of colloidal silica;

"Silsesquioxane cocondensates" are cocondensates of dialkoxysilanes and trialkoxysilanes;

"Substrate" means a solid layer;

"Support structure" means any system, device, part, or combination of parts for supporting a lens;

"Transparent" means exhibiting a luminous transmittance value of at least 85% when tested in accordance with ASTM D 1003-00;

"Welding helmet" means a helmet that has a lens that is dark or can darken to protect the wearer's eyes from light transmitted by a welding machine; and "Derived from" means prepared from.

DETAILED DESCRIPTION OF PREFERRED EMBODIMENTS

The full-face respiratory mask, welding helmet, or face shield includes a lens that includes a low surface energy hard-coat layer. The lens optionally includes a primer disposed on the lens between the lens and the hard-coat layer. The hard-coat layer preferably is in contact with the primer layer.

The lens is suitable for use in a full-face respiratory mask, welding helmet, or face shield. The low surface energy outer surface may be an integral part of the hard-coat layer—that is, the hard-coat layer may provide abrasion resistance and low surface energy features—or the low surface energy outer surface may be a separate layer. The surface energy refers to the balance between forces of cohesion (of a material with itself) and adhesion (of a material to another material). In general, liquids that come in contact with a material that has a low surface energy will bead up on the surface rather than wetting it. One method of measuring surface energy of a surface involves determining the angle of contact between the solid surface and a liquid drop, as described below under "Method of Measuring Contact Angle." The surface of the hard-coat layer preferably exhibits a static water contact angle of at least 95 degrees, at least 100 degrees, or even at least 105 degrees and a static hexadecane contact angle of at least 50 degrees, at least 60 degrees, or even at least 65 degrees.

Figure 1:
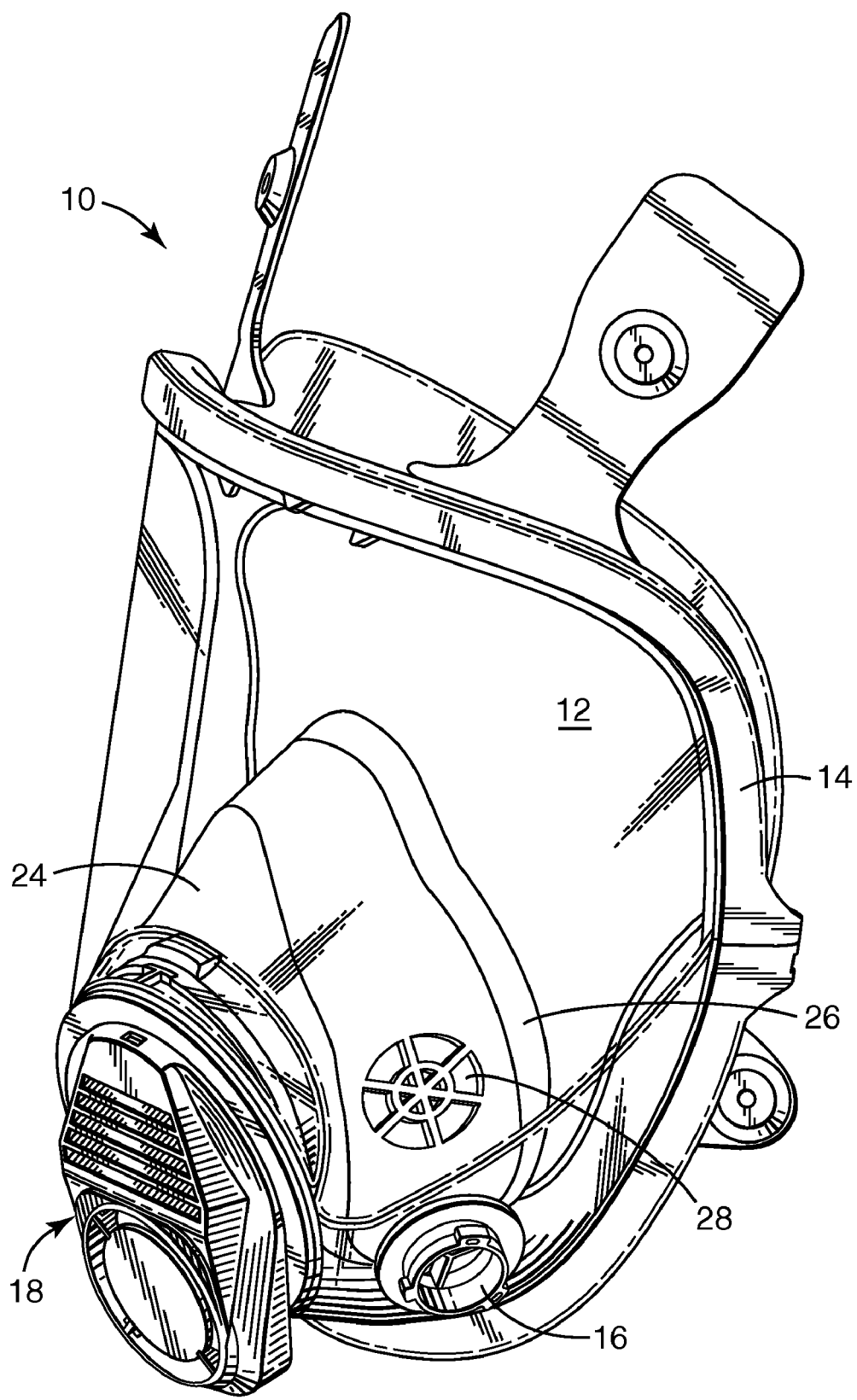
FIG. 1 is a perspective view of a full-face respirator 10 that has a lens 12 in accordance with the present invention.

FIG. 1 illustrates a full-face respiratory mask 10 that has a lens 12 supported thereon for allowing a wearer of the respirator to see the surrounding environment. The lens 12 is transparent and provides the wearer with sufficient visibility to see objects located in front of the wearer and also preferably to the side of the wearer with little head rotation. The front surface of the lens 12 has a hard-coat layer located on it to protect the lens from abrasion that could result in the workplace. The hard-coat layer is disposed on an underlying substrate, e.g., plastic. The hard-coat layer is provided with a low surface energy outer surface to protect the lens from being stained from various sprays and solvents that may be used in the workplace. The full-face respirator 10 also includes a support structure such as frame 14 for supporting the lens 12 on the respirator 10. The respirator 10 also may include one or more filter cartridges for providing clean air to the wearer. The filter cartridges attach to the respirator 10 at ports 16. The filter cartridges may be configured as shown, for example, in U.S. Pat. No. 6,277,178 or in U.S. Pat. RE39493, and incorporated herein. Alternatively, a clean air supply can be attached to an inlet port 16 on the respiratory mask 10 to provide the wearer with a supply of clean air. The clean air supply could be a powered air purifying system (see, for example, U.S. Pat. No. 6,895,960 (Fabin)) or it could be a self-contained breathing apparatus that uses a pressurized system such as a pressurized tank. The respirator 10 may also have an exhalation valve system 18 for allowing exhaled air to exit the interior gas space of the full-face respirator 10. The exhalation valve typically includes a diaphragm that opens in response to pressure from exhaled air. The diaphragm may include a flexible flap that lifts from a seal surface in response to increased pressure within the interior gas space of the mask. Exhaled air can be first centralized within a nose cup 24. The nose cup 24 may include a compliant face-contacting member 26 and an inhalation valve 28. The inhalation valve 28 closes when a person exhales so that exhaled air does not fog the lens 12. Exhaled air thereby passes through the exhalation valve 18 to enter the exterior gas space. Examples of other full-face respiratory masks that may be used in connection with the present invention are shown in U.S. Pat. No. 5,924,420 (Reischel et al.), U.S. Pat. No. 6,763,835 (Grove et al.), U.S. Pat. No. 5,303,701 (Heins et al.), and U.S. Pat. No. 6,978,782 (Tayebi), and incorporated herein.

Figure 2:
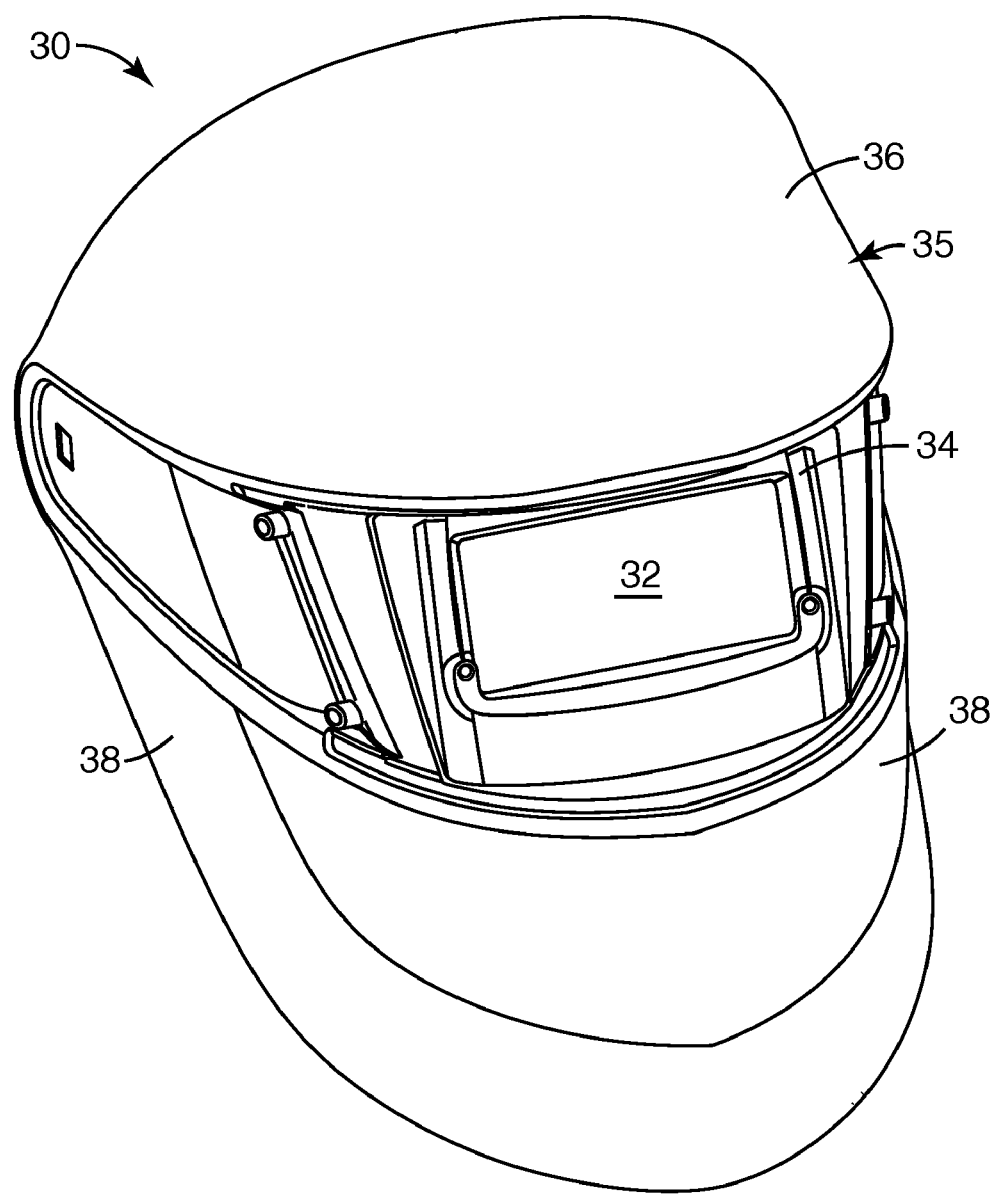
FIG. 2 is a perspective view of a welding helmet 30 that has a lens 32 in accordance with the present invention.

FIG. 2 shows a welding helmet 30 that includes a lens 32 for allowing a wearer of the helmet to see the surrounding environment. Often, the lens in a welding helmet is an auto-darkening lens that darkens upon exposure to light from a welding torch. When in a darkened state, welding helmet wearers can still see the working environment but their eyes are protected from the glow of the torch. An example of an auto-darkening lens is described in U.S. Pat. No. 5,825,441 (Hornell et al.) and incorporated herein. Like full-face respiratory masks, welding helmets also can be exposed to materials that can have a deleterious effect on the ability of the lens to provide a clear viewing screen. The lens 32 has a support structure such as a frame 34 for supporting it on the welding helmet 30. The welding helmet 30 also has an outer shell structure 35 that includes top and side panels 36 and 38, respectively, for protecting the top and sides of the wearer's head. To support the welding helmet 30 on a wearer's head, the welding helmet 30 may further include a harness or crown member that rests upon the top of a person's head and is connected to the outer shell structure 35. Usually the outer shell structure 35 will pivot upwardly so that the wearer can lift the helmet above the wearer's face when not in use. An example of such a head harness is shown in U.S. Pat. No. 5,191,468 (Mases). Examples of other welding helmets that may be suitable for use in connection with the present invention are shown in U.S. Pat. No. 6,055,666 (Eklund et al.), U.S. Pat. No. 3,868,727 (Paschall), U.S. Pat. No. 4,707,860 (Holstrom), and U.S. Pat. No. 4,863,244 (Fuerthbauer et al.), and incorporated herein.

Figure 3:
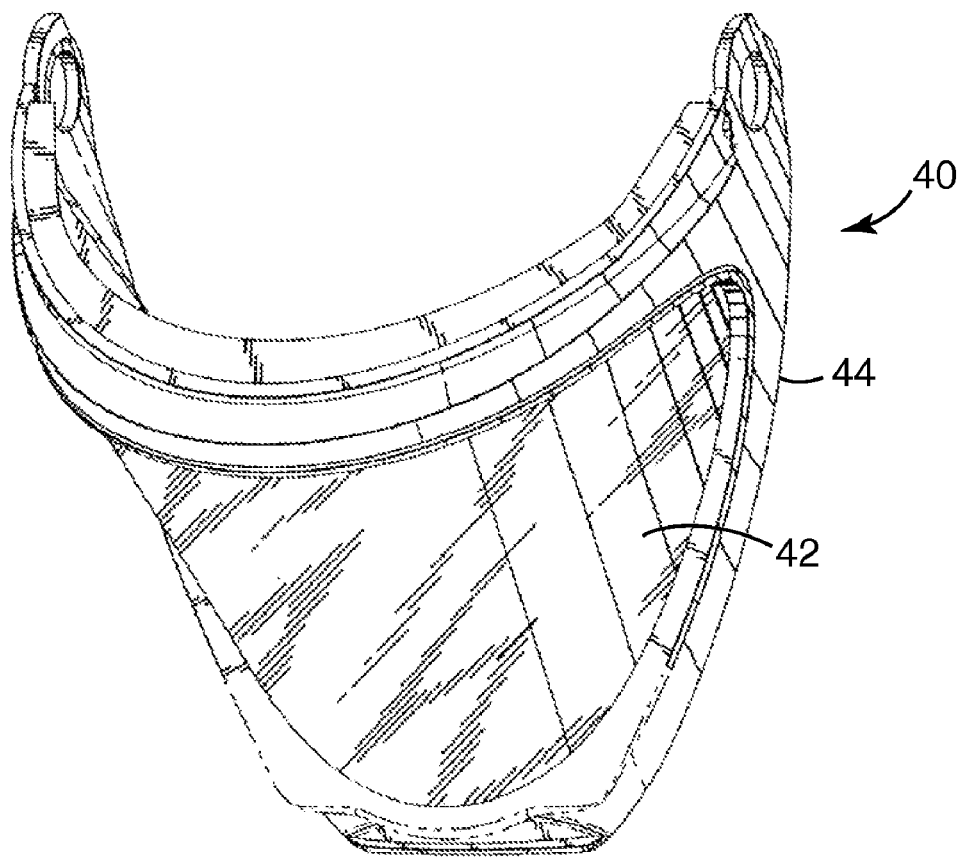
FIG. 3 is a perspective view of a face shield 40 that has a lens 42 in accordance with the present invention.

FIG. 3 illustrates a face shield 40 that has a lens 42 through which a wearer can see the surrounding environment. A frame 44 surrounds the lens 42 at its perimeter. Other face shields have been disclosed in U.S. Pat. No. 7,077,128 to Wilson et al., U.S. Pat. No. 5,446,926 to Baker et al., U.S. Pat. No. 5,303,423 to Gazzara et al., Des. 416,649 to Burns et al., and EP U.S. Pat. No. 1,410,775A2 to Kjell et al.

Figure 4:
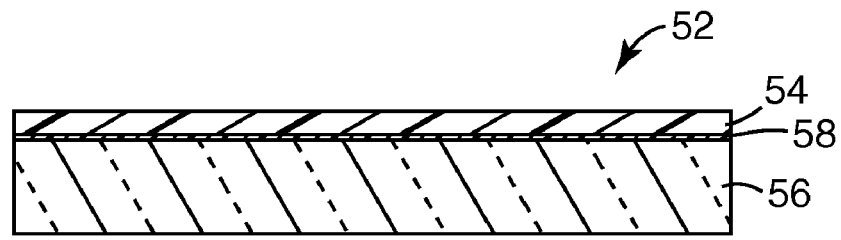
FIG. 4 is a cross-section of a lens 52 that has a hard-coat layer 54 located thereon in accordance with the present invention.

FIG. 4 illustrates a cross-sectional view of a lens 52 that includes a hard-coat layer 54 disposed on a substrate 56. A primer layer 58 is located between the substrate 56 and the hard-coat layer 54 to enable a good bond to exist between those two layers.

The lens can be formed from any suitable material including, e.g., plastic (e.g., polycarbonate, poly(methylmethacrylate), polyethylene, polypropylene, polyethylene terephthalate, polystyrene, and combinations thereof), various inorganic materials including, e.g., glass and sapphire, and combinations thereof.

The hard-coat layer preferably exhibits oil- and water-repellency properties, stain-release, stain-resistance characteristics, or a combination thereof. The hard-coat layer includes the reaction product of an additive and a silsesquioxane-based hard-coat composition. The hard-coat coating composition from which the hard-coat layer is derived preferably includes additive in an amount from about 0.01% by weight to about 10% by weight, from about 0.1% by weight to about 1% by weight, or even from about 0.2% to about 0.5% by weight based on the total solids content of the hard-coat composition, and silsesquioxane-based hard-coat composition in an amount from about 50% by weight to about 99.99% by weight, from about 90% by weight to about 99.99% by weight, from about 99% by weight to about 99.9% by weight, or even from about 99.5% by weight to about 99.8% by weight based on the total solids content of the hard-coat coating composition.

A variety of additives are suitable for inclusion in the hard-coat composition including, e.g., perfluoropolyether urethanes that include hydrolysable silane groups, fluorochemical oligomers including, e.g., acrylate polymers that include at least one perfluoropolyether moiety and at least one hydrolysable silane group, and mixtures thereof. Examples of suitable additives are described in more detail below.

One useful class of additives includes perfluoropolyether urethanes that include hydrolysable silane groups of Formula (1)

  (1)

wherein
$R_f$ is a fluorine-containing group that includes a perfluorooxyalkyl group or a perfluorooxyalkylene group,
$R^1$ is the residue of a polyisocyanate having a valence of x+y,
$R^1$ is a silane-containing moiety of the formula:

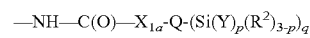

wherein
Q is a connecting group of valency at least 2
$X^{1a}$ is O, S, or NR, wherein R is H, aryl, a lower alkyl of 1 to 4 carbon atoms, or $Q\text{-}(Si(Y)_p(R^2)_{3-p})_q$,
Y is a hydrolysable group,
$R^2$ is a monovalent alkyl or aryl group,
p is 1, 2 or 3, and
q is from 1 to 6,
x and y are each independently at least 1, and
z is at least 1.

One useful example of an additive of Formula (1) has the Formula (1A):

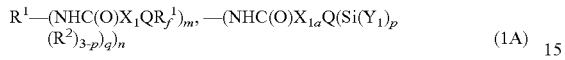
$$R^1\text{—}(NHC(O)X_1QR_f^1)_m, \text{—}(NHC(O)X_{1a}Q(Si(Y_1)_p(R^2)_{3-p})_q)_n \quad (1A)$$

wherein
$R_i$ is a residue of a multi-isocyanate,
$X_1$ is O, S, or NR, wherein R is H, aryl, or a lower alkyl of 1 to 4 carbon atoms,
$X_{1a}$ is O, S, or NR, wherein R is H, aryl, a lower alkyl of 1 to 4 carbon atoms, or $Q\text{-}(Si(Y_1)_p(R^2)_{3-p})_q$,
$R_f^1$ is a monovalent perfluoropolyether moiety that includes groups of the formula $F(R_{fc}O)_wC_dF_{2d}\text{—}$
wherein
each $R_{fc}$ independently represents a fluorinated alkylene group having from 1 to 6 carbon atoms,
each w independently represents an integer of at least 2, and
d is an integer from 1 to 6,
Q is independently a connecting group of valency at least 2,
$Y_1$ is a hydrolysable group selected from —$OR_2$ and —$OC(O)R_2$, wherein $R_2$ is a lower alkyl of 1 to 4 carbon atoms,
$R^2$ is a monovalent alkyl or aryl group,
m is at least 1,
n is at least 1,
p is 1, 2 or 3,
q is from 1 to 6,
m+n is from 2 to 10, and
each unit referred to by the subscripts m and n is attached to an $R^1$ unit.

Q can be a straight or branched chain or cycle-containing connecting group. Q can include a covalent bond, an alkylene, an arylene, an aralkylene, or an alkarylene. Q can optionally include heteroatoms such as O, N, and S, and combinations thereof. Q can also optionally include a heteroatom-containing functional group such as carbonyl or sulfonyl, and combinations thereof.

By their method of synthesis, the additives of Formula (1) are necessarily mixtures. In Formula (1A), for example, if the mole fraction of isocyanate groups is arbitrarily given a value of 1.0, then the total mole fraction of m and n units used in making the additive of Formula (1A) is at least 1.0. The mole fractions of m:n are from 0.95:0.05 to 0.05:0.95, from 0.50:0.50 to 0.05:0.95, from 0.25:0.75 to 0.05:0.95 or even from 0.25:0.75 to 0.10:0.95. In the instances the mole fractions of m:n total more than one, such as 0.15:0.90, the m unit is reacted onto the isocyanate first, and a slight excess (e.g., 0.05 mole fraction) of the n units are used.

In a formulation, for instance, in which 0.15 mole fractions of m and 0.85 mole fraction of n units are introduced, a distribution of products is formed in which some fraction of products formed contain no m units. There will, however, be present in this product distribution, the additives of Formulas (1) and (1A).

A variety of compounds that include hydrolysable silane groups that are isocyanate reactive, or that may add free-radically or in Michael fashion to unsaturated double bonds, are suitable including, e.g., $H_2N(CH_2)_3Si(OCH_3)_3$, $H(CH_3)N(CH_2)_3Si(OCH_3)_3$, $HS(CH_2)_3Si(OCH_3)_3$, and $HN((CH_2)_3Si(OCH_3)_3)_2$.

Additionally, there is another class of isocyanate reactive oligomers that include hydrolysable silane groups that are of the Formula (OSi), which can be used in making materials of Formula (1), $$X\text{-}M^h_{j1}M^a_{k1}S\text{-}Q^1\text{-}OH(OSi),$$

wherein
X represents the residue of an initiator or hydrogen,
$M^h$ represents units derived from non-fluorinated monomers,
$M^a$ represents units derived from monomers having a silyl group represented by the formula $$Si(Y_1)_p(R^2)_{3-p},$$

wherein
$Y_1$ is a hydrolysable group selected from the group of —$OR_2$ and —$OC(O)R_2$, wherein $R_2$ is a lower alkyl of 1 to 4 carbon atoms,
$R^2$ is a monovalent alkyl or aryl group, and
p is 1, 2 or 3,
$Q^1$ is a divalent organic linking group
j1 is 0 to 20, and
k1 is 2 to 20.

Useful $M^h$ monomers include acrylates, including, e.g., octadecyl acrylate, methyl acrylate, ethyl acrylate, and butyl acrylate.

Useful $M^a$ monomers include, e.g., vinyltrimethoxysilane, vinyltriethoxysilane, and alkoxysilane functionalized acrylates and methacrylates, including, e.g., methacryloyloxypropyl trimethoxysilane.

An oligomer of Formula (OSi) can be obtained in a variety of ways including, e.g., by polymerizing three moles of $H_2C{=}C(CH_3)C(O)O(CH_2)_3Si(OCH_3)$ with one mole of $HSCH_2CH_2CH_2OH$ with a thermal initiator (e.g., VAZO-67 thermal initiator, which is commercially available from DuPont), in a nitrogen degassed solvent such as ethyl acetate, at about 70° C. for ten hours.

One useful example of an additive of Formula (1) is an additive having the Formula (1A')

$$R_i\text{—}(NHC(O)X_1QR_f^1)_m, \text{—}(O\text{-}Q^1\text{-}S\text{-}M^h_{j1}M^a_{k1}X)_n \quad (1A')$$

wherein all groups are as defined above.

Additionally, a variety of compounds that include hydrolysable silane groups that are isocyanate reactive may be used to replace a portion of the oligomer of Formula (OSi) to make the perfluoropolyether urethanes with hydrolysable silane groups that are partially derived from an oligomer of the formula (OSi). Examples of such compounds include $H_2N(CH_2)_3Si(OCH_3)_3$, $H(CH_3)N(CH_2)_3Si(OCH_3)_3$, $HS(CH_2)_3Si(OCH_3)_3$, and $HN((CH_2)_3Si(OCH_3)_3)_2$.

One useful method of making the additive of Formula (1) includes first reacting the polyisocyanate with the nucleophilic fluorine-containing compound (e.g., a perfluoropolyether-containing alcohol, thiol, or amine), followed by reaction with the alcohol, thiol, or amine functional silane, usually in a non-hydroxylic solvent and in the presence of a catalyst such as an organotin compound.

Another useful method of making the additive of Formula (1) includes reacting the polyisocyanate with the alcohol, thiol, or amine functional silane, followed by reaction with the nucleophilic fluorine-containing compound, usually in a non-hydroxylic solvent and in the presence of a catalyst such as an organotin compound. In addition, the additives could be made by reacting all three components simultaneously, usually in a non-hydroxylic solvent and in the presence of a catalyst such as an organotin compound.

Another example of an additive of Formula (1) is shown below as structure (1B):

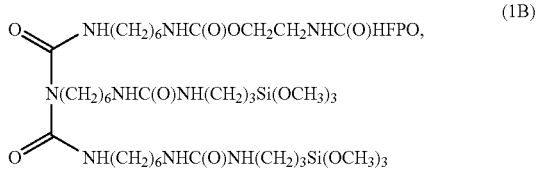

which is the reaction product of the biuret of 1,6-hexamethylene diisocyanate (HDI) with one equivalent of HFPO oligomer amidol (e.g., $F(CF(CF_3)CF_2O)_{xx}CF(CF_3)C(O)NHCH_2CH_2OH$, where the average value of xx is about 6.5), followed by reaction with two equivalents of 3-aminopropyl trimethoxysilane. Another example of an additive of Formula (1) is shown below as structure (1C):

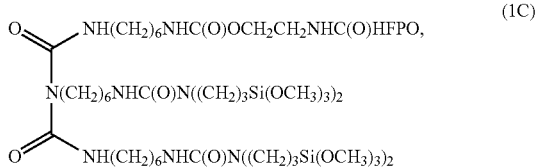

which is the reaction product of the biuret of HDI with one equivalent of HFPO oligomer amidol (e.g., $F(CF(CF_3)CF_2O)_{xx}CF(CF_3)C(O)NHCH_2CH_2OH$, where the average value of xx is about 6.5), followed by reaction with two equivalents of bis(3- trimethoxysilylpropyl) amine.

Useful additives of Formula (1) and methods of making the same are disclosed in published U.S. Patent Application Nos. 2005/0054804 A1 (Dams, et. al.), 2005/0121644 A1 (Dams, et al.), U.S. Pat. No. 7,097,910 (Moore et. al.) and 2004/014718 A1 (Johnson et. al.), and incorporated herein.

Another example of an additive of Formula (1) is the class of perfluoropolyether urethanes that include hydrolysable silane groups of Formula (1D)

wherein
$R_f$ is a fluorine-containing group that includes a perfluorooxyalkyl group or a perfluorooxyalkylene group,
$R^1$ is the residue of a polyisocyanate having a valency of x+y,
$R^B$ is of the formula

wherein
$X_1$ is O, S, or NR, wherein R is H, aryl, or a lower alkyl of 1 to 4 carbon atoms,
$R^3$ is a polyvalent group that includes alkylene, arylene or a combination thereof (e.g., an alkarylene group), the alkylene group optionally including at least one catenary oxygen atom,
$R^5$ is a divalent alkylene group, the alkylene group optionally including at least one catenary oxygen atom,
Y is a hydrolysable group,
$R^2$ is a monovalent alkyl or aryl group,
p is 1, 2 or 3, and
q is 1 to 6,
x and y are each independently at least 1, and
z is at least 1.

The perfluoropolyether urethane of Formula (1D) is derived from, in part, a nucleophilic ethylenically unsaturated compound having an isocyanate-reactive, nucleophilic functional group and at least one ethylenically unsaturated group (hereinafter a "nucleophilic unsaturated compound"). The ethylenically unsaturated group may be a vinyl, allyl or allyloxy and the nucleophilic functional group may be an amino or hydroxy group. Preferably the ethylenically unsaturated group is not a vinyloxy group, e.g. $CH_2=CHO-$. Preferably, the nucleophilic unsaturated compound is a polyunsaturated compound having a hydroxyl group and at least two unsaturated groups. Such compounds include compounds of the Formula (1a):

wherein
$X_1$ is O, S, or NR, wherein R is H, aryl, or a lower alkyl of 1 to 4 carbon atoms,
$R^3$ is a polyvalent group that includes alkylene, arylene or a combination thereof (e.g., an alkarylene group), the alkylene group optionally includes at least one catenary oxygen atom, and
q is 1 to 6, preferably greater than 1.

The resulting nucleophilic polyunsaturated compounds allow the addition of multiple silane groups to the urethane compound. The molar ratio of silane groups to $-NH-C(O)-X_1-$ groups may be greater than 1:1, or greater than 2:1. Preferably $HX_1-$ is not directly connected to an aromatic ring, such as a phenolic compound.

Compounds of Formula (1a) include, e.g., terminally mono-, di- or poly-unsaturated ethers of polyols such as 1,3-butylene glycol, 1,4-butanediol, 1,6-hexanediol, cyclohexane dimethanol, neopentyl glycol, caprolactone modified neopentylglycol hydroxypivalate, diethylene glycol, dipropylene glycol, bisphenol-A, trimethylolpropane, neopentyl glycol, tetraethylene glycol, tricyclodecanedimethanol, triethylene glycol, tripropylene glycol, glycerol, pentaerythritol, and dipentaerythritol.

Useful nucleophilic unsaturated compounds include, e.g., hydroxyalkenes such as allyl alcohol, methallyl alcohol, allyloxyethyl alcohol, 2-allyloxymethylpropanol (from dimethylolethane), and 2,2-di(allyloxymethyl)butanol (from trimethylolpropane), as well as the corresponding amines.

The nucleophilic unsaturated compound of Formula (1a), and the nucleophilic fluorine-containing compound, may react with the isocyanate groups of the polyisocyanate to form a perfluoropolyether urethane compound having pendent unsaturated groups, which may subsequently be reacted with a thiosilane to form a compound of Formula (1D).

The reaction product of the nucleophilic unsaturated compound, and the nucleophilic fluorine-containing compound with the polyisocyanate is of the general Formula (1b):

wherein
$R_f$ is a fluorine-containing group that includes a perfluorooxyalkyl group or a perfluorooxyalkylene group,
$R^6$ is the residue of a polyisocyanate, $X_1$ is O, S, or NR, wherein R is H, aryl, or a lower alkyl of 1 to 4 carbon atoms, $R^3$ is a polyvalent group that includes alkylene, arylene or a combination thereof (e.g., an alkarylene group), the alkylene group optionally includes at least one catenary oxygen atom, x is 1 or 2, z is at least 1, q is 1 to 6, preferably 2 to 5.

The perfluoropolyether urethane compounds include, in part, the free radical addition reaction product of a thiosilane with an unsaturated group of the compounds of Formulas (1a) or (1b). The thiosilane is of the Formula (1c)

wherein $R^5$ is a divalent alkylene group, the alkylene group optionally including catenary oxygen atoms, Y is a hydrolysable group, $R^2$ is a monovalent alkyl or aryl group, p is 1, 2 or 3, and Y represents a hydrolysable group in Formula (1c) such as, for example, a halide, a $C_1$-$C_4$ alkoxy group, an acyloxy group or a polyoxyalkylene group such as polyoxyethylene groups, as disclosed, e.g., in U.S. Pat. No. 5,274,159 and incorporated herein. $R^2$ preferably is non-hydrolysable.

The thiosilane can be reacted with the nucleophilic unsaturated compound of Formula (1a) to form an addition product, which may subsequently be reacted with the polyisocyanate (either before or after functionalization by the nucleophilic fluorinated compound). Alternatively, the nucleophilic unsaturated compound of Formula (1a) can first be reacted with a polyisocyanate to form a urethane compound of Formula (1b), followed by free-radical addition of the thiosilane to the ethylenically unsaturated groups pendent from the urethane compound. Preferably, the nucleophilic unsaturated compound is first reacted with the polyisocyanate (again, before or after reaction with the nucleophilic fluorinated compound) to form a urethane compound having pendent unsaturated groups, to which is added the thiosilane by free radical addition.

Useful thiosilanes include (mercaptomethyl)dimethylethoxysilane, (mercaptomethyl)methyldiethoxysilane, 3-mercaptopropylmethyldimethoxysilane, and 3-mercaptopropyltriethoxysilane.

The addition of the mercaptosilane of Formula (1c) to the ethylenically unsaturated compounds of Formula (1a) or (1b) may be effected using free radical initiators. Useful free radical initiators include inorganic and organic peroxides, hydroperoxides, persulfates, azo compounds, redox systems (e.g., a mixture of $K_2S_2O_8$ and $Na_2S_2O_5$), and free radical photoinitiators such as those described by K. K. Dietliker in Chemistry & Technology of UV & EB Formulation for Coatings, Inks & Paints, Volume 3, pages 276-298, SITA Technology Ltd., London (1991) and incorporated herein. Useful examples include hydrogen peroxide, potassium persulfate, t-butyl hydroperoxide, benzoyl peroxide, t-butyl perbenzoate, cumene hydroperoxide, 2,2'-azobis(2-methylbutyronitrile), (VAZO 67), and azobis(isobutyronitrile) (AIBN). The skilled artisan will recognize that the choice of initiator will depend upon the particular reaction conditions including, e.g., choice of solvent.

The free-radical addition of the thiosilane can add to either the least substituted carbon atom of the ethylenically unsaturated group or to a more highly substituted carbon atom of the ethylenically unsaturated group.

The perfluoropolyether urethane compounds can be made by blending the nucleophilic unsaturated compound(s), fluorine-containing nucleophilic compound(s), and the polyisocyanate compound(s), followed by free-radical addition of the thiosilanes to the unsaturated groups. As one skilled in the art would understand, the order of blending or the ordering of the steps is non-limiting and can be modified so as to produce a desired perfluoropolyether urethane compounds. In one embodiment, for example, the polyisocyanate compound(s) and the nucleophilic fluorochemical compound are first reacted with some portion of the isocyanate groups, followed by reaction of the nucleophilic unsaturated compound(s) with some portion of the remaining isocyanate groups, followed by free-radical addition of the thiosilane to the pendent unsaturated groups.

One example of a useful additive of Formula (1D) is shown below as the structure of Formula (1E):

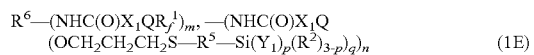

wherein all groups are as defined above.

Another example of a useful the additive of Formula (1D) is shown below as the structure of Formula (1F):

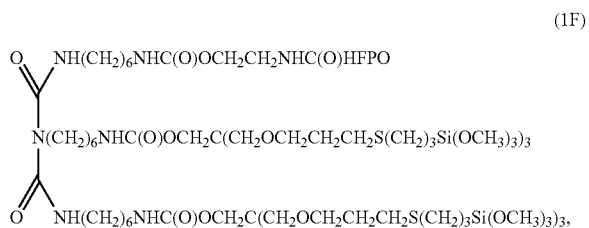

which can be obtained by the reaction of the biuret of 1,6-hexamethylene diisocyanate (HDI) with one equivalent of HFPO oligomer amidol (e.g., $F(CF(CF_3)CF_2O)_{xx}CF(CF_3)C(O)NHCH_2CH_2OH$, where the average value of xx is about 6.5), followed by reaction with pentaerythritol triallyl ether, followed by free radical addition of $HS(CH_2)_3Si(OCH_3)_3$ to the allyl ethers.

Other useful examples of the additive of Formula (1D) are disclosed in U.S. Provisional application No. 60/870,300, filed Dec. 15, 2006, and incorporated herein.

Another example of an additive of Formula (1) includes the class of perfluoropolyether urethanes that include hydrolysable silane groups of Formula (1G)

wherein $R_f$ is a fluorine-containing group that includes a perfluorooxyalkyl group or a perfluorooxyalkylene group, $R^1$ is the residue of a polyisocyanate having a valency of x+y, $R^C$ is a silane-containing moiety derived from the Michael reaction between a nucleophilic acryloyl compound and an aminosilane, x and y are each independently at least 1, and z is at least 1.

Preferably $R^C$ is of the formula

wherein $R^4$ is $R^3Si(Y)_p(R^2)_{3-p}$ or $R^2$, $X_2$ is —O— or —S—, preferably —O, and all other groups are defined as above.

One example of a useful additive according to Formula (1G) is the additive of Formula (1H):

$$R^6-(NHC(O)X_1QR_f^1)_m, -(NHC(O)X_2QX_1(C(O)CH_2CH_2-NR_4R^3Si(Y_1)_p(R^2)_{3-p})_q)_n \quad (1H),$$

wherein all groups are as defined above.

The additive of Formula (1G), is derived, in part, from a nucleophilic acryloyl compound having an isocyanate-reactive, nucleophilic functional group and at least one acryloyl group (hereinafter a "nucleophilic acryloyl compound"). The acryloyl moiety may be an acrylate or acrylamide, and the nucleophilic functional group may be an amino or hydroxy group. Preferably, the nucleophilic acryloyl compound is a polyacryl compound having a hydroxyl group and at least two acryloyl groups.

Such compounds include those of the Formula (1I):

$$HX_2-R^3-(X_1-C(O)CH=CH_2)_q \quad (1I),$$

wherein all groups are as defined above.

The resulting multiple acryloyl groups allow the addition of multiple silane groups to the urethane compound. The molar ratio of silane groups to —NH—C(O)—$X_1$— groups may be greater than 1:1, or even greater than 2:1. Preferably $HX_1$— is not directly connected to an aromatic ring, such as with a phenolic compound.

Useful nucleophilic acryloyl compounds include, e.g., acrylate compounds including, e.g., (a) monoacryloyl containing compounds such as hydroxyethyl acrylate, glycerol monoacrylate, 1,3-butylene glycol monoacrylate, 1,4-butanediol monoacrylate, 1,6-hexanediol monoacrylate, alkoxylated aliphatic monoacrylate, cyclohexane dimethanol monoacrylate, alkoxylated hexanediol monoacrylate, alkoxylated neopentyl glycol monoacrylate, caprolactone modified neopentylglycol hydroxypivalate monoacrylate, diethylene glycol monoacrylate, dipropylene glycol monoacrylate, ethoxylated bisphenol-A monoacrylate, hydroxypivalaldehyde modified trimethylolpropane monoacrylate, neopentyl glycol monoacrylate, propoxylated neopentyl glycol monoacrylate, tetraethylene glycol monoacrylate, tricyclodecanedimethanol monoacrylate, triethylene glycol monoacrylate, and tripropylene glycol monoacrylate, (b) multiacryloyl-containing compounds such as glycerol diacrylate, ethoxylated triacrylates (e.g., ethoxylated trimethylolpropane diacrylate), pentaerythritol triacrylate, propoxylated diacrylates (e.g., propoxylated (3) glyceryl diacrylate, propoxylated (5.5) glyceryl diacrylate, propoxylated (3) trimethylolpropane diacrylate, propoxylated (6) trimethylolpropane diacrylate), trimethylolpropane diacrylate, higher functionality (meth)acryl containing compounds such as di-trimethylolpropane triacrylate, and dipentaerythritol pentaacrylate. Such compounds are widely available from vendors such as, e.g., Sartomer Company (Exton, Pa.), UCB Chemicals Corporation (Smyrna, Ga.), and Aldrich Chemical Company (Milwaukee, Wis.). Additional useful acrylate materials include dihydroxyhydantoin moiety-containing polyacrylates as described, e.g., in U.S. Pat. No. 4,262,072 (Wendling et al.).

With respect to the exemplary nucleophilic acryloyl compounds, it will be understood that the corresponding acrylamides may be used. Further, the indicated hydroxyl groups may be substituted by the corresponding thiol group.

The additives of Formula (1G) include, in part, the Michael reaction product of an aminosilane with an acryloyl group. The aminosilane may be reacted with the nucleophilic acryloyl compound to form a Michael adduct, which can subsequently be reacted with the polyisocyanate (either before or after functionalization by the nucleophilic fluorochemical compound). Preferably, the nucleophilic acryloyl compound is first reacted with the polyisocyanate (again, before or after reaction with the nucleophilic fluorochemical compound), to form a urethane compound having pendent acryloyl groups, to which is added the aminosilane by Michael addition.

Preferred aminosilanes may be represented by the general Formula (1J):

$$HN(R_5)-R^3-Si(Y)_p(R^2)_{3-p} \quad (1J),$$

wherein $R_5$ is $R^3Si(Y)_p(R^2)_{3-p}$, H, or $R^2$, p is 1, 2 or 3, preferably 3, and all other groups are defined as above.

With respect to the aminosilanes of Formula (1J), it should be noted that primary amines, those wherein $R_5$ is H, are capable of reacting with two acryloyl groups by Michael addition, which may lead to crosslinking of the additive of Formula (1G). Further, primary amines may also compete with the Michael addition of the aminosilane to the acryloyl groups. For these reasons, $R_5$=H is not preferred, although 20 mole percent of such primary aminosilanes may be used.

Some useful aminosilanes are described in U.S. Pat. No. 4,378,250 (Treadway et al.) and incorporated herein by reference, and include, e.g., N-methylaminopropyltrimethoxysilane, bis(3-trimethoxysilylpropyl)amine, 3-aminopropylmethyl diethoxysilane, 2-aminoethyltriethoxysilane, 2-aminoethyltrimethoxysilane, 2-aminoethyltributoxysilane, 2-aminoethyltripropoxysilane, 2-aminoethyltriethoxysilane, 3-aminopropyltrimethoxysilane, 3-aminopropyltriethoxysilane, 3-aminopropyltributoxysilane, and 3-aminopropyltripropoxysilane.

Minor amounts (i.e., less than 20 mole percent) of catenary nitrogen-containing aminosilanes may also be used, including those described, e.g., in U.S. Pat. No. 4,378,250 (Treadway et al.) and incorporated herein by reference. Useful catenary nitrogen-containing aminosilanes include, e.g., N-(2-aminoethyl)-2-aminoethyltrimethoxysilane, N-(2-aminoethyl)-2-aminoethyltriethoxysilane, N-(2-aminoethyl)-2-aminoethyltripropoxysilane, N-(2-aminoethyl)-3-aminopropyltrimethoxysilane, N-(2-aminoethyl)-3-aminopropyltriethoxysilane, N-(2-aminoethyl)-3-aminopropyltripropoxysilane, N-(3-aminopropyl)-2-aminoethyltrimethoxysilane, N-(3-aminopropyl)-2-aminoethyltriethoxysilane, and N-(3-aminopropyl)-2-aminoethyltripropoxysilane.

The additive of Formula (1K), a precursor of Formula (1G), can be made by simple blending of the nucleophilic acryloyl compound(s), fluorine-containing nucleophilic compound(s), and the polyisocyanate compound(s), wherein Formula (1K) is:

$$(R_f)_x\text{-}[R^6NHC(O)X_2-R^3-(X_1C(O)CH=CH_2)_q]_z \quad (1K)$$

wherein $R_f$ is a fluorine-containing group that includes a perfluorooxyalkyl group or a perfluorooxyalkylene group, $R^6$ is the residue of a polyisocyanate, $X_2$ is —O— or —S—, $X_1$ is O, S, or NR, wherein R is H, aryl, or a lower alkyl of 1 to 4 carbon, $R^3$ is a polyvalent group that includes alkylene, arylene or a combination thereof (e.g., an alkarylene group), the alkylene group optionally including at least one catenary oxygen atoms, x is 1 or 2, q is 1 to 6, and z is at least 1.

This is followed by Michael addition of the aminosilanes of Formula (1J) to the acryloyl groups of Formula (1K). The order of blending or the ordering of the steps is non-limiting and can be modified so as to produce a desired additive of Formula (1G).

In a preferred embodiment, the polyisocyanate compound(s) and the fluorine-containing nucleophilic compound of Formula (1N) (set forth below) are first reacted with some portion of the isocyanate groups whereby pendent fluorine-containing groups are thereby bonded to the isocyanate functional urethane compounds. This is followed by reaction of the nucleophilic acryloyl compound(s) of Formula (1I) with some portion of the remaining isocyanate groups, followed by Michael addition of the aminosilane of Formula (1J) to the pendent acryloyl groups.

In general, the reactive components and a solvent are charged to a dry reaction vessel in immediate succession or as pre-made mixtures. When a homogeneous mixture or solution is obtained a catalyst is optionally added, and the reaction mixture is heated at a temperature, and for a time sufficient for the reaction to occur. Progress of the reaction can be determined by monitoring the disappearance of the isocyanate peak in the IR.

The nucleophilic compound $R_f^2$-$[Q(X_1H)_y]_z$ of Formula (1N) (set forth below) is used in an amount sufficient to react with from about 5 mole percent to about 50 mole percent of the available isocyanate functional groups. Preferably a compound of Formula (1N) is used to react with from about 10 mole percent to about 30 mole percent of the isocyanate groups. The remaining isocyanate groups, from about 50 mole percent to about 95 mole percent or even from about 70 mole percent to about 90 mole percent, are functionalized by the nucleophilic acryloyl compound of Formula (1I), followed by Michael addition of the aminosilane of Formula (1J), resulting in a urethane compound having both pendent fluorochemical groups and pendent hydrolysable silane groups.

Alternatively, the aminosilane of Formula (1J) and the nucleophilic acryloyl compound of Formula (1I) may be pre-reacted to form the Michael adduct of Formula (1L)

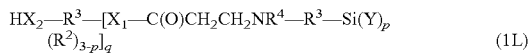
$$HX_2-R^3-[X_1-C(O)CH_2CH_2NR^4-R^3-Si(Y)_p(R^2)_{3-p}]_q \quad (1L)$$

wherein all groups are defined as above.

This Michael adduct of Formula (1L), wherein the groups are defined as above, is reacted with the remaining isocyanate groups of the product resulting from the reaction of the polyisocyanate compounds and fluorine containing nucleophilic compound of Formula (1N). The fluorochemical urethane, corresponding to Formula (1G), generally has essentially no remaining isocyanate groups by IR.

Another example of the additive of Formula (1G) is shown below as structure (1M):

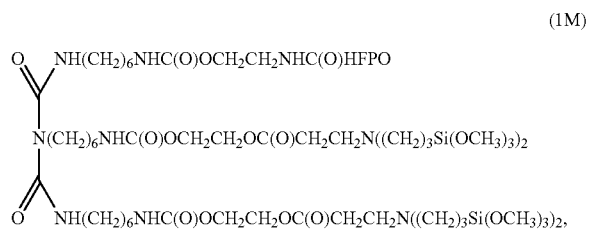
(1M)

which is the reaction product of the biuret of HDI with one equivalent of HFPO oligomer amidol (e.g., $F(CF(CF_3)CF_2O)_{xx}CF(CF_3)C(O)NHCH_2CH_2OH$, where the average value of xx is about 6.5), followed by reaction with two equivalents of hydroxyethylacrylate, followed by Michael reaction of the acrylate groups with bis(3-trimethoxysilylpropyl)amine.

Other useful examples of the additive of Formula (1G) are disclosed in which is U.S. provisional application No. 60/871,034, filed Dec. 20, 2006, and incorporated herein.

Although no catalyst is required for the Michael addition of the aminosilanes to the acryloyl groups, suitable catalysts for the Michael reaction include a base of which the conjugated acid preferably has a pKa between 12 and 14. The base preferably is organic. Examples of such bases include 1,4-dihydropyridines, methyl diphenylphosphane, methyl di-p-tolylphosphane, 2-allyl-N-alkyl imidazolines, tetra-t-butylammonium hydroxide, DBU (1,8-diazabicyclo[5.4.0]undec-7-ene) and DBN (1,5-diazabicyclo[4.3.0]non-5-ene), potassium methoxide, sodium methoxide, and sodium hydroxide. A preferred catalyst is DBU and tetramethylguanidine. The amount of catalyst used in the Michael addition reaction is preferably from about 0.05% by weight to about 2% by weight or even from about 0.1% by weight to about 1.0% by weight based on solids.

Polyisocyanate compounds useful in preparing the additive of Formulas (1) through (1H), and (1M) include isocyanate radicals attached to the multivalent organic groups ($R^1$), ($R^1$) or ($R^6$) that can include a multivalent aliphatic, alicyclic, or aromatic moiety, or a multivalent aliphatic, alicyclic or aromatic moiety attached to a biuret, an isocyanurate, or a uretdione, and mixtures thereof. Preferred polyfunctional isocyanate compounds include an average of at least two isocyanate (—NCO) radicals. Compounds that include at least two —NCO radicals preferably include di- and trivalent aliphatic, alicyclic, araliphatic, or aromatic groups to which the —NCO radicals are attached. Aliphatic di- or trivalent groups are preferred.

Representative examples of suitable polyisocyanate compounds include isocyanate functional derivatives of the polyisocyanate compounds as defined herein. Useful isocyanate functional derivatives include, e.g., ureas, biurets, allophanates, dimers, and trimers (such as uretdiones and isocyanurates) of isocyanate compounds, and mixtures thereof. Any suitable organic polyisocyanate including, e.g., aliphatic, alicyclic, araliphatic, and aromatic polyisocyanates, can be used either singly or in mixtures of at least two.

Suitable aromatic polyisocyanate compounds include, e.g., 2,4-toluene diisocyanate (TDI), 2,6-toluene diisocyanate, an adduct of TDI with trimethylolpropane (commercially available under the DESMODUR CB trade designation from Bayer Corporation, (Pittsburgh, Pa.)), the isocyanurate trimer of TDI (commercially available under the DESMODUR IL trade designation from Bayer Corporation (Pittsburgh, Pa.), diphenylmethane 4,4'-diisocyanate (MDI), diphenylmethane 2,4'-diisocyanate, 1,5-diisocyanato-naphthalene, 1,4-phenylene diisocyanate, 1,3-phenylene diisocyanate, 1-methoxy-2,4-phenylene diisocyanate, 1-chlorophenyl-2,4-diisocyanate, and mixtures thereof.

Examples of useful alicyclic polyisocyanate compounds include dicyclohexylmethane diisocyanate ($H_{12}$ MDI), which is commercially available under the DESMODUR trade designation from Bayer Corporation, 4,4'-isopropyl-bis(cyclohexylisocyanate), isophorone diisocyanate (IPDI), cyclobutane-1,3-diisocyanate, cyclohexane 1,3-diisocyanate, cyclohexane 1,4-diisocyanate (CHDI), 1,4-cyclohexanebis (methylene isocyanate) (BDI), dimer acid diisocyanate (available from Bayer Corporation), 1,3-bis(isocyanatomethyl)cyclohexane ($H_6$ XDI), 3-isocyanatomethyl-3,5,5-trimethylcyclohexyl isocyanate, and mixtures thereof.

Examples of useful aliphatic polyisocyanate compounds include tetramethylene 1,4-diisocyanate, hexamethylene 1,4- diisocyanate, hexamethylene 1,6-diisocyanate (HDI), octamethylene 1,8-diisocyanate, 1,12-diisocyanatododecane, 2,2,4-trimethyl-hexamethylene diisocyanate (TMDI), 2-methyl-1,5-pentamethylene diisocyanate, dimer diisocyanate, the urea of hexamethylene diisocyanate, the biuret of hexamethylene 1,6-diisocyanate (HDI) (e.g., commercially available under the DESMODUR N-100 and N-3200 trade designations from Bayer Corporation), the isocyanurate of HDI (commercially available under the DESMODUR N-3300 and DESMODUR N-3600 trade designations from Bayer Corporation), a blend of the isocyanurate of HDI and the uretdione of HDI (commercially available under the DESMODUR N-3400 trade designation from Bayer Corporation), and mixtures thereof.

Examples of useful araliphatic polyisocyanates include m-tetramethyl xylylene diisocyanate (m-TMXDI), p-tetramethyl xylylene diisocyanate (p-TMXDI), 1,4-xylylene diisocyanate (XDI), 1,3-xylylene diisocyanate, p-(1-isocyanatoethyl)phenyl isocyanate, m-(3-isocyanatobutyl)phenyl isocyanate, 4-(2-isocyanatocyclohexyl-methyl)phenyl isocyanate, and mixtures thereof.

Preferred polyisocyanates include, e.g., tetramethylene 1,4-diisocyanate, hexamethylene 1,4-diisocyanate, hexamethylene 1,6-diisocyanate (HDI), octamethylene 1,8-diisocyanate, 1,12-diisocyanatododecane, and mixtures thereof.

Additives of Formulas (1) through (1H), and (IM) that include compounds or oligomers made with the preferred polyisocyanates set forth above impart both high water and hexadecane contact angles, which are typically predictive of good water-repellency and oil-repellency properties.

The additives of Formulas (1) through (1H), and (IM) include, in part, the reaction product of a fluorochemical compound having a mono- or difunctional perfluorinated group, and at least one nucleophilic, isocyanate-reactive functional group. Such compounds include those of Formula (1N):

$$R_f^2\text{-}[Q(X_1H)_y]_z \quad (1N)$$

wherein $R_f^2$ is a monovalent perfluorooxyalkyl group (wherein z is 1), or a divalent perfluorooxyalkylene group (wherein z is 2), and all other groups are defined as above.

Useful perfluorooxyalkyl and perfluorooxyalkylene $R_f^2$ groups correspond to the Formula (1O):

$$W\text{—}R_f^3\text{—}O\text{—}R_f^4\text{—}(R_f^5)_{q1} \quad (10)$$

wherein

W is F for monovalent perfluorooxyalkyl and an open valence ("—") for divalent perfluorooxyalkylene, $R_f^3$ represents a perfluoroalkylene group, $R_f^3$ represents a perfluoroalkyleneoxy group consisting of perfluoroalkyleneoxy groups having 1, 2, 3 or 4 carbon atoms or a mixture of such perfluoroalkyleneoxy groups, $R_f^5$ represents a perfluoroalkylene group, and q1 is 0 or 1.

The perfluoroalkylene groups $R_f^3$ and $R_f^5$ in Formula (10) can be linear or branched and can include from 1 to 10 carbon atoms, or even from 1 to 6 carbon atoms. One example of a useful monovalent perfluoroalkyl group is $CF_3$—$CF_2$—$CF_2$—. Examples of useful divalent perfluoroalkylene groups include —$CF_2$—$CF_2$—$CF_2$—, —$CF_2$—, and —$CF(CF_3)$ $CF_2$—.

The perfluoroalkyleneoxy group $R_f^4$ can include the same perfluoroalkyleneoxy units or of a mixture of different perfluoroalkyleneoxy units. When the perfluoroalkyleneoxy group includes different perfluoroalkyleneoxy units, the units can be present in a random configuration, alternating configuration or as blocks. Useful examples of perfluoroalkyleneoxy groups include —$[CF_2$—$CF_2$—$O]_r$—; —$[CF(CF_3)$—$CF_2$—$O]_s$—, —$[CF_2CF_2$—$O]_r$—$[CF_2O]_t$—, —$[CF_2CF_2CF_2CF_2$—$O]_u$, and —$[CF_2$—$CF_2$—$O]_r$—$[CF(CF_3)$—$CF_2$—$O]_s$—, wherein each of r, s, t and u is an integer of from 1 to 50 or even from 2 to 25. A preferred perfluorooxyalkyl group that corresponds to Formula (10) is $CF_3$—$CF_2$—$CF_2$—O—$[CF(CF_3)$—$CF_2O]_s$—$CF(CF_3)CF_2$— wherein s is an integer from 2 to 25.

Perfluorooxyalkyl and perfluoroxyalkylene compounds can be obtained by the oligomerization of hexafluoropropylene oxide that results in a terminal carbonyl fluoride group. This carbonyl fluoride may be converted into an acid, ester or alcohol by reactions well known to those skilled in the art. The carbonyl fluoride or acid, ester or alcohol derived therefrom may then be reacted further to introduce the desired isocyanate reactive groups according to known procedures.

With respect to Formulas (1), (1D) and (1G), wherein y or z is 1, fluorochemical monofunctional compounds, preferably monoalcohols and monoamines, are contemplated. Representative examples of useful fluorochemical monofunctional compounds include $C_3F_7C(O)N(H)CH_2CH_2OH$; $C_3F_7O(CF(CF_3)CF_2O)_{1-36}CF(CF_3)CH_2OH$ and $C_3F_7O(CF(CF_3)CF_2O)_{1-36}CF(CF_3)C(O)N(H)CH_2CH_2OH$, and mixtures thereof. If desired, other isocyanate-reactive functional groups may be used in place of those depicted.

With respect to Formulas (1), (1D) and (1G), wherein y or z is 2, fluorinated polyols are preferred. Representative examples of suitable fluorinated polyols include $CF_3CF_2(OCF_2CF_2)_3OCF_2C(O)N(CH_3)CH_2CH(OH)CH_2OH$, FOMBLIN ZDOL $HOCH_2CF_2O(CF_2O)_{8-12}(CF_2CF_2O)_{8-12}CF_2CH_2OH$ (which is commercially available from Solvay-Solexis, Milan, Italy), $HOCH_2CF(CF_3)O(CF(CF_3)CF_2O)_{1-36}CF(CF_3)CH_2OH$, and $HOCH_2CH_2N(H)C(O)CF(CF_3)O(CF(CF_3)CF_2O)_{1-36}CF(CF_3)C(O)N(H)CH_2CH_2OH$.

Depending on reaction conditions (e.g., reaction temperature and/or the type and amount of polyisocyanate used), a catalyst level of no greater than about 0.5% by weight, from about 0.00005% by weight to about 0.5% by weight, or even from about 0.02% by weight to 0.1% by weight of the reaction mixture may be used to effect the condensation reactions with the isocyanates. In general, if the nucleophilic group is an amine group, a catalyst is not necessary.

Suitable catalysts include, e.g., tertiary amine and tin compounds. Examples of useful tin compounds include tin II and tin IV salts such as stannous octoate, dibutyltin dilaurate, dibutyltin diacetate, dibutyltin di-2-ethylhexanoate, and dibutyltinoxide. Examples of useful tertiary amine compounds include triethylamine, tributylamine, triethylenediamine, tripropylamine, bis(dimethylaminoethyl)ether, morpholine compounds such as ethyl morpholine and 2,2'-dimorpholinodiethyl ether, 1,4-diazabicyclo[2.2.2]octane (an example of which is available under the DABCO trade designation from Aldrich Chemical Co. (Milwaukee, Wis.)), and 1,8-diazabicyclo[5.4.0.]undec-7-ene (an example of which is available under the DBU trade designation from Aldrich Chemical Co.). Tin compounds are preferred. If an acid catalyst is used, it is preferably removed from the product or neutralized after the reaction.

Useful additives of the acrylate polymers that include at least one perfluoropolyether moiety and at least one hydrolysable silane group type include the class of acrylate polymers of Formula (2):

$$X\text{-}M^f{}_iM^h{}_jM^a{}_k\text{-}G \quad (2)$$

wherein

X represents the residue of an initiator or hydrogen, $M^f$ represents units derived from fluorinated monomers, $M^h$ represents units derived from non-fluorinated monomers, $M^a$ represents units having a silyl group represented by the formula $$Si(Y_1)_p(R^2)_{3-p},$$

wherein
- $Y_1$ is a hydrolysable group selected from the group of $-OR_2$ and $-OC(O)R_2$, wherein $R_2$ is a lower alkyl of 1 to 4 carbon atoms,
- $R^2$ is a monovalent alkyl or aryl group, and
- p is 1, 2 or 3, G is a monovalent organic group that includes the residue of a chain transfer agent, i represents a value of 1 to 100, j represents a value of 0 to 100, k represents a value of 0 to 100, and i+j+k is at least 2, with the proviso that at least one of the following conditions is fulfilled,
- a) G is a monovalent organic group that includes a silyl group of the formula $$Si(Y_1)P(R^2)_{3-p},$$

wherein
- $Y_1$ is a hydrolysable group selected from $-OR_2$ and $-OC(O)R_2$, wherein $R_2$ is a lower alkyl of 1 to 4 carbon atoms,
- $R^2$ is a monovalent alkyl or aryl group, and
- p is 1, 2 or 3, and
- b) k is at least 1.

In some embodiments, G corresponds to the Formula (2A):

$$-SQ^1T^2C(O)NHQ^5Si(Y_1)(Y^2)(Y^3)- \quad (2A),$$

wherein
- $Q^1$ and $Q^5$ each independently represent an organic divalent linking group,
- T2 represents O or NR with R being hydrogen, an aryl or a $C_1$-$C_4$ alkyl group, and
- $Y^1$, $Y^2$ and $Y_3$ each independently represent an alkyl group, an aryl group or a hydrolysable group with at least one of $Y^1$, $Y^2$ and $Y_3$ representing a hydrolysable group.

The units $M^f$ of the fluorochemical silane are generally derived from fluorochemical monomers corresponding to the Formula (2B)

$$R_f\text{-}Q\text{-}E^1 \quad (2B),$$

wherein
- $R_f$ is a fluorine-containing group that includes a perfluorooxyalkyl group or a perfluorooxyalkylene group,
- Q is independently a connecting group of valency at least 2, and
- $E^1$ represents a free radical polymerizable group.

Examples of suitable fluorochemical monomers include $C_3F_7O(CF(CF_3)CF_2O)_uCF(CF_3)CH_2OC(O)CH=CH_2$, $C_3F_7O(CF(CF_3)CF_2O)_uCF(CF_3)CH_2OC(O)C(CH_3)=CH_2$, $CH_2=CHC(O)OCH_2CF_2(OCF_2)_u(OCF_2CF_2)_v$ $OCF_2CH_2OC(O)CH=CH_2$, and $CH_2=C(CH_3)C(O)$ $OCH_2CF_2(OCF_2)_u(OCF_2CF_2)_vOCF_2CH_2OC(O)C(CH_3)=$ $CH_2$, wherein u and v are independently 1 to 50.

The units $M^h$ of the fluorochemical silane (when present) are generally derived from a non-fluorinated monomer, preferably a monomer consisting of a polymerizable group and a hydrocarbon moiety. Hydrocarbon containing monomers are well known and generally commercially available. Useful hydrocarbon containing monomers include those monomers according to Formula (2C):

$$R^h\text{-}(Q^6)_S\text{-}E^3 \quad (2C),$$

wherein
- $R^1$ represents a hydrocarbon group,
- $Q^6$ is a divalent linking group,
- s is 0 or 1, and
- $E^3$ is a free radical polymerizable group.

Illustrative examples of useful linking groups $Q^6$ include oxy, carbonyl, carbonyloxy, carbonamido, sulphonamido, oxyalkylene, and poly(oxyalkylene). Illustrative examples of non-fluorinated monomers from which the units $M^h$ can be derived include general classes of ethylenic compounds capable of free-radical polymerization including, for example, allyl esters (e.g., allyl acetate and allyl heptanoate), alkyl vinyl ethers and alkyl allyl ethers (e.g., cetyl vinyl ether, dodecylvinyl ether, 2-chloroethylvinyl ether, and ethylvinyl ether), unsaturated acids such as acrylic acid, methacrylic acid, alpha-chloro acrylic acid, crotonic acid, maleic acid, fumaric acid, itaconic acid, and their anhydrides and their esters such as vinyl, allyl, methyl, butyl, isobutyl, hexyl, heptyl, 2-ethylhexyl, cyclohexyl, lauryl, stearyl, and isobornyl, and alkoxy ethyl acrylates and methacrylates, alpha-beta unsaturated nitriles, such as acrylonitrile, methacrylonitrile and 2-chloroacrylonitrile, 2-cyanoethyl acrylate and alkyl cyanoacrylates, alpha,beta-unsaturated carboxylic acid derivatives such as allyl alcohol, allyl glycolate, acrylamide, methacrylamide, n-diisopropyl acrylamide, diacetoneacrylamide, N,N-diethylaminoethylmethacrylate, N-n-butylaminoethyl methacrylate, N-t-butylaminoethyl methacrylate, styrene and its derivatives such as vinyltoluene, alpha-methylstyrene, and alpha-cyanomethyl styrene, lower olefinic hydrocarbons, which can contain halogen such as ethylene, propylene, isobutene, 3-chloro-1-isobutene, butadiene, and isoprene, chloro and dichlorobutadiene and 2,5-dimethyl-1,5-hexadiene, and allyl or vinyl halides such as vinyl and vinylidene chloride. Preferred non-fluorinated monomers include hydrocarbon group containing monomers such as octadecylmethacrylate, laurylmethacrylate, butylacrylate, N-methylol acrylamide, isobutylmethacrylate, ethylhexyl acrylate and ethylhexyl methacrylate, vinylchloride and vinylidene chloride.

The fluorochemical silane generally further includes units $M^a$ that have a silyl group that has at least one hydrolysable group. Illustrative examples of useful $M^a$ units include those units that correspond to the general Formula (2D):

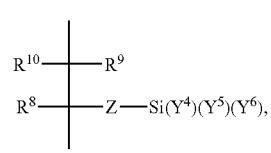

(2D)

wherein
- $R^8$, $R^9$ and $R^{10}$ each independently represent hydrogen, an alkyl group (e.g., methyl and ethyl), a halogen, or an aryl group,
- Z represents an organic divalent linking group, and
- $Y^4$, $Y^5$ and $Y^6$ independently represent an alkyl group, an aryl group, or a hydrolysable group.

Examples of useful monomers according to Formula (2D) include vinyltrichlorosilane, vinyltrimethoxysilane, vinyltriethoxysilane, and alkoxysilane functionalized acrylates and methacrylates, such as methacryloyloxypropyl trimethoxysilane.

The fluorochemical silane can be prepared through a free radical polymerization of a fluorinated monomer, optionally with a non-fluorinated monomer and a monomer that includes the silyl group, in the presence of a chain transfer agent. A free radical initiator can be used to initiate the polymerization or oligomerization reaction. Suitable free-radical initiators include, e.g., azo compounds, such as azobisisobutyronitrile (AIBN) and azo-2-cyanovaleric acid, hydroperoxides (e/g/. cumene, t-butyl and t-amyl hydroperoxide, dialkyl peroxides such as di-t-butyl and dicumylperoxide), peroxyesters such as t-butylperbenzoate and di-t-butylperoxy phthalate, diacylperoxides such as benzoyl peroxide and lauroyl peroxide.

The oligomerization reaction can be carried out in any solvent suitable for organic free-radical reactions. The reactants can be present in the solvent at any suitable concentration including, e.g., from about 5% by weight to about 90% by weight based on the total weight of the reaction mixture. Suitable solvents include, e.g., aliphatic and alicyclic hydrocarbons (e.g., hexane, heptane, cyclohexane), aromatic solvents (e.g., benzene, toluene, xylene), ethers (e.g., diethylether, glyme, diglyme, diisopropyl ether), esters (e.g., ethyl acetate, butyl acetate), alcohols (e.g., ethanol, isopropyl alcohol), ketones (e.g., acetone, methylethyl ketone, methyl isobutyl ketone), sulfoxides (e.g., dimethyl sulfoxide), amides (e.g., N,N-dimethylformamide, N,N-dimethylacetamide), halogenated solvents such as methylchloroform, FREON 113, trichloroethylene, alpha,alpha,alpha-trifluorotoluene, and mixtures thereof.

The oligomerization reaction can be carried out at any temperature suitable for conducting an organic free-radical reaction. Particular temperature and solvents for use can be easily selected based on considerations such as the solubility of reagents, the temperature required for the use of a particular initiator, and desired molecular weight. While it is not practical to enumerate a particular temperature suitable for all initiators and all solvents, generally suitable temperatures are from about 30° C. and about 200° C.

The fluorochemical oligomer is prepared in the presence of chain transfer agent. Suitable chain transfer agents include, e.g., a hydroxy-, amino-, mercapto and halogen groups. The chain transfer agent can include at least two of such hydroxy, amino-, mercapto and halogen groups. Illustrative examples of chain transfer agents useful in the preparation of the fluorochemical oligomer include 2-mercaptoethanol, 3-mercapto-2-butanol, 3-mercapto-2-propanol, 3-mercapto-1-propanol, 3-mercapto-1,2-propanediol, 2-mercapto-ethylamine, di(2-mercaptoethyl)sulfide, octylmercaptan, and dodecylmercaptan.

In one useful embodiment, a chain transfer agent that includes a silyl group having at least one hydrolyzable groups is used in the oligomerization to produce the fluorochemical oligomer. Useful chain transfer agent that include such a silyl group include chain transfer agents of Formula (2E):

$$HLSi(Y^1)(Y^2)(Y^3) \quad (2E),$$

wherein

L represents a divalent linking group, and $Y^1$, $Y^2$ and $Y^3$ each independently represents an alkyl group, preferably a $C_1$-$C_8$ alkyl group such as methyl, ethyl and propyl, an alkyl group containing a cycloalkyl such as cyclohexyl and cyclopentyl, an aryl group such as phenyl, an alkylaryl group, an aralkyl group, and a hydrolysable group such as a halogen or an alkoxy group such as methoxy, ethoxy or an aryloxy group, where at least one of $Y^1$, $Y^2$ and $Y^3$ represents a hydrolysable group.

A single chain transfer agent or a mixture of different chain transfer agents can be used. Useful chain transfer agents are 2-mercaptoethanol, octylmercaptane and 3-mercaptopropyl-trimethoxysilane. A chain transfer agent is preferably present in an amount sufficient to control the number of polymerized monomer units in the oligomer and to obtain the desired molecular weight of the oligomeric fluorochemical silane. The chain transfer agent is generally used in an amount of about 0.05 equivalents to about 0.5 equivalents, preferably about 0.25 equivalents, per equivalent of monomer including fluorinated and non-fluorinated monomers. One example of a useful commercially available chain transfer agent is A-160 $HS(CH_2)_3Si(OCH_3)_3$ from Sigma-Aldrich Chemical Company (Milwaukee, Wis.).

Suitable compounds for reacting with the functional groups included in the monomer or chain transfer agent include compounds according to the following Formula (2F)

$$A-Q^5Si(Y^1)(Y^2)(Y^3) \quad (2F)$$

wherein

A represents a functional group capable of undergoing a condensation reaction with the functional group contained in the monomer or chain transfer agent, in particular a functional group capable of condensing with a hydroxy or amino functional oligomer (examples of A include an isocyanate or an epoxy group), $Q^5$ represents an organic divalent linking group, and $Y^1$, $Y^2$ and $Y_3$ are as defined above.

The organic divalent linking groups $Q^5$ preferably include from 1 to about 20 carbon atoms. $Q^5$ can optionally include oxygen, nitrogen, or sulfur-containing groups or a combination thereof. Illustrative examples of suitable linking groups $Q^5$ include straight chain, branched chain and cyclic alkylene, arylene, aralkylene, oxyalkylene, carbonyloxyalkylene, oxycarboxyalkylene, carboxyamidoalkylene, urethanylenealkylene, ureylenealkylene, and combinations thereof. Preferred linking groups include alkylene, oxyalkylene and carbonyloxyalkylene.

Examples of useful compounds according to Formula (2F) include 3-isocyanatopropyltrimethoxysilane and 3-epoxypropyltrimethoxysilane. When a hydroxy or amino functionalized chain transfer agent is used that is subsequently reacted with a compound according to Formula (2F) wherein A is an isocyanato group, the resulting monovalent organic group G in the fluorochemical compound can generally be represented by the Formula (2H).

$$-SQ^1T^2C(O)NHQ^5Si(Y^1)(Y^2)(Y^3) \quad (2H)$$

wherein $Q^1$, $Q^5$, $Y^1$, $Y^2$ and $Y^3$ are as defined above, and $T^2$ represents O or NR with R being hydrogen, an aryl or a $C_1$-$C_4$ alkyl group.

Other useful additives according to Formula (2) and methods of making the same are described, e.g., in U.S. Pat. No. 7,166,329 and incorporated herein.

Other useful compositions and additives suitable for use in hard-coat compositions are disclosed in U.S. Pat. No. 7,097,910, U.S. Publication Nos. 2004/0147188-A1, 2005/0121644-A1, and 2006/0216524-A1, and U.S. Ser. Nos. 60/871,034 and 60/870,300, and incorporated herein.

Although the inventors do not wish to be bound by theory, the additives of Formulas (1) and (2) are believed to undergo a condensation reaction with themselves and the silsesquioxane-based hard-coat composition to form a crosslinked siloxane layer via hydrolysis or displacement of their hydrolysable "Y" groups. In this context, "siloxane" refers to —Si—O—Si— structural units to which are attached compounds of Formulas (1) and (2). In the presence of water, the "Y" groups will undergo hydrolysis to "Si—OH" groups, and further condensation to siloxanes. If the substrate has functionality reactive with hydrolysable or hydrolyzed silane groups, as is the case with glass surfaces, the additives, silsesquioxane-based hard-coat composition, and combinations thereof may also form covalent bonds with the surface.

A hard-coat prepared from a hard-coat composition that includes the additive of Formulas (1) and (2) includes the additives of Formulas (1) and (2) per se, as well as siloxane derivatives that form from the additives of Formulas (1) and (2) by themselves, from the silsesquioxane-based hard-coat composition, and from a combination of the additives of Formulas (1) and (2) and the silsesquioxane-based hard-coat composition. The hard-coat can also include unreacted or uncondensed "Si—Y" groups, non-silane materials such as oligomeric perfluorooxyalkyl monohydrides, starting materials, perfluorooxyalkyl alcohols, esters and combinations thereof.

Silsesquioxane

Useful silsesquioxane-based hard-coat compositions include, e.g., condensates of trialkoxysilanes (or hydrolysates thereof) and colloidal silica; co-condensates of diorganooxysilanes of the formula $R^{12}{}_2Si(OR^{13})_2$ (or hydrolysates thereof), trialkoxysilanes (or hydrolysates thereof), and colloidal silica; and mixtures thereof. The condensates and co-condensates are of the formula $R^{12}SiO_{3/2}$, wherein each $R^{12}$ is an alkyl group of from 1 to 6 carbon atoms or an aryl group, and $R^{13}$ is an alkyl radical having from 1 to 4 carbon atoms. A useful method of making the silsesquioxane-based hard-coat compositions includes hydrolysis of the alkoxysilanes in the presence of colloidal silica dispersion and in a mixture of water and alcoholic solvents. The colloidal silica dispersions preferably have a particle size from 5 nm to 150 nm, or even from 10 nm to 30 nm. Useful colloidal silica dispersions are commercially available under a variety of trade designations from E. I. duPont and Nalco Chemical including the LUDOX trade designation from E. I. duPont de Nemours and Co., Inc. (Wilmington, Del.) and the NALCO trade designation from Nalco Chemical Co. (Oak Brook, Ill.). Useful silsesquioxanes can be made by a variety of techniques including the techniques described in U.S. Pat. No. 3,986,997 (Clark), U.S. Pat. No. 4,624,870 (Anthony), and U.S. Pat. No. 5,411,807 (Patel et al.), and incorporated by reference. The silsequioxane-based hard-coat composition is present in the hard-coat composition in an amount of from about 90% by weight to about 99.9% by weight based on the total solids of the hard-coat composition.

Another useful method of preparing a silsesquioxane-based hard-coat composition includes adding hydrolysable silane to a mixture of colloidal silica dispersion, water and optionally materials such as surface active agent and organic water-miscible solvent, while agitating the mixture under acidic or basic conditions. The exact amount of silane that can be added depends on the substituent R and whether an anionic or cationic surface-active agent is used. Co-condensates of the silsesquioxanes in which the units can be present in block or random distribution are formed by the simultaneous hydrolysis of the silanes. The amount of tetraorganosilanes (including, e.g., tetralkoxysilanes and hydrosylates thereof (e.g. tetraalkoxysilanes of the formula $Si(OH)_4$, and oligomers thereof) present is less than 10% by weight, less than 5% by weight, or even less than about 2% by weight based on the solids of the silsequioxane-based hard-coat composition. After hydrolysis is complete, the product may be diluted with additional solvent, and additives may be added. Suitable additives include, e.g., UV absorbers, buffers (e.g., methyltriacetoxysilane (e.g., for silsesquioxane-based hard-coat compositions that are made with basic colloidal silica), antioxidants, cure catalysts (e.g., amine carboxylates such as ethylamine carboxylate and quaternary ammonium carboxylates such as benzyltrimethylammonium acetate), and combinations thereof.

Silanes useful in preparing the silsesquioxane-based hard coat compositions include, e.g., methyltrimethoxysilane, methyltriethoxysilane, methyltriisopropoxyoxysilane, ethyltrimethoxysilane, ethyltriethoxysilane, propyltrimethoxysilane, isobutyltrimethoxysilane, isobutyltriethoxysilane, 2-ethylbutyltriethoxysilane, 2-ethylbutoxytriethoxysilane, and combinations thereof.

Optional Additives

The hard-coat coating composition can optionally include other additives including, e.g., solvents (i.e., an organic solvent), water and acid. In some embodiments, the hard-coat coating composition includes a mixture of the additive and a solvent. Particularly useful solvents include, e.g., organic solvents including, e.g., alcohols (e.g., methanol, ethanol, isopropanol and diacetone alcohol), toluene, ketones (e.g., methyl ethyl ketone), esters, glycol ethers, amides, hydrocarbons, hydrofluorocarbons, hydrofluoroethers, chlorohydrocarbons, chlorocarbons, ethers such as tetrahydrofuran, water, and mixtures thereof. Trialkoxysilanes such as methyltrimethoxysilane and tetraalkoxysilanes such as tetraethoxysilane may also be added.

The hard-coat coating composition can exist in a variety of forms including, e.g., solvent or aqueous suspensions, dispersions and solutions of the additive and the silsesquioxane-based hard coat composition. In addition, the additive can be dissolved, suspended, or dispersed in a variety of solvents prior to or after combination with the silsesquioxane-based hard-coat composition. Useful hard-coat coating compositions in the form of solvent solutions include from about 0.1% by weight to about 50% by weight, or even no greater than about 90% by weight solvent based on the total weight of the composition. The hard-coat coating composition preferably includes from about 0.1% by weight to about 10% by weight, from about 0.1% by weight to about 5% by weight or even from about 0.2% by weight to about 1% by weight additive based on total solids.

For ease of manufacturing and for reasons of cost, the hard-coat coating composition can be prepared shortly before use by diluting a concentrate of at least one of the additives disclosed herein. The concentrate will generally include a concentrated solution of the additive in an organic solvent. The concentrate is preferably stable for several weeks, at least 1 month, or even at least 3 months. Many of the additives can readily dissolve in an organic solvent at high concentrations. The diluted concentrate can then be combined with the silsesquioxane-based hard-coat composition prior to use.

Method of Use

The hard-coat coating composition is suitable for use in a method of coating that includes contacting a substrate with a hard-coat coating composition that includes the additive, the silsesquioxane-based hard-coat composition, a solvent, and optionally water and an acid. In one embodiment the method includes contacting a substrate with a hard-coat coating composition that includes the additive and a solvent, and subsequently contacting the substrate with an aqueous acid.

The hard-coat coating composition can be applied to a substrate using any suitable method or technique including, e.g., spraying, brushing, wiping, knife coating, notch coating, reverse roll coating, gravure coating, soaking, dip coating, bar coating, flood coating, spin coating and combinations thereof, and in any suitable form including a continuous or discontinuous layer. The resulting hard-coat can likewise exist in a variety of forms including, e.g., a continuous or discontinuous layer (e.g., in a pattern, dots, stripes and swirls)

and can be the result of multiple layers disposed on top of one another. The resulting hard-coat is relatively durable, more resistant to contamination, and easier to clean relative to the substrate surface without the hard-coat.

The hard-coat composition can be applied at any thickness to provide the desired level of water, oil, stain, and soil repellency. The hard-coat is preferably present on a substrate in an amount that does not substantially change the appearance and optical characteristics of the underlying substrate. Typically, if the hard-coat coating composition is to be used as the sole hard-coat, the thickness of the dried cured coating is from 1 micron to 100 microns, from 1 micron to 10 microns, or even from 2 microns to 5 microns. If the hard-coat coating composition is applied as the top layer of at least two layers (e.g., the at least two layers may be of a composition that is the same or different from each other and from the hard-coat coating composition), the hard-coat top layer may be applied as a much thinner layer. Such hard-coat top layer, when dry, may be of a thickness of, e.g., 20 Angstroms to 1 micron, or even from 40 nanometers to 100 nanometers. A useful total thickness for the hard-coat (which includes all layers in a multiple layer coating) can be any suitable thickness including, e.g., from about 1 micron to about 5 microns.

The hard-coat coating composition can be coated on a substrate (e.g., a lens (e.g., plastic or glass)) and at least partially cured (e.g., dried, crosslinked, and combinations thereof) to provide a coated article. Any optional solvent present is typically at least partially removed (e.g., using a forced air oven, through evaporation at elevated temperature, through evaporation at ambient temperatures, and combinations thereof), and the composition is then at least partially cured to form a durable coating.

A preferred method of coating the hard-coat coating composition includes dip coating. A substrate to be coated can be contacted with the hard-coat coating composition at room temperature (typically, about 20° C. to about 25° C.). Alternatively, the hard-coat coating composition can be applied to a substrate that has been preheated at an elevated temperature including, e.g., from 60° C. to 150° C. This is of particular interest for industrial production where substrates can be treated immediately after the baking oven at the end of the production line. Following application, the treated substrate can be dried and cured at ambient or elevated temperature including, e.g. from about 40° C. to about 300° C. and for a time sufficient to dry. The process may also require a polishing step.

The hard-coat coating composition can also be coated on a primed surface of a substrate (e.g., a lens, a plastic substrate or a glass substrate). Examples of suitable primer compositions include poly(methyl methacrylate) primers, examples of which are commercially available under the SHC401 series of trade designations from Silicone division of General Electric Company, now Momentive Performance Materials, Inc. (Friendly, W. Va.). Other useful primer compositions and methods of making the same are described, e.g., in U.S. Pat. No. 5,041,313 (Patel) and incorporated herein. The primer layer can be in the form of a continuous or discontinuous layer (e.g., in a pattern, dots, stripes and swirls), a single layer, multiple primer layers disposed on top of one another, and combinations thereof.

The invention will now be described by the following Examples. Unless otherwise indicated to the contrary, all weights are based on percent by weight.

EXAMPLES

Test Methods

Nuclear Magnetic Resonance (NMR)

$^1$H and $^{19}$F NMR spectra are run on a Varian UNITYplus 400 Fourier transform NMR spectrometer (available from Varian NMR Instruments, Palo Alto, Calif.).

IR Spectroscopy (IR)

IR spectra are run on a Thermo-Nicolet, Avatar 370 FTIR, obtainable from Thermo Electron Corporation, Waltham, Mass.

Ink Repellency Test

This test is used to measure the ink repellency of the coatings on polycarbonate plaques. Coated polycarbonate plaques are prepared as described above. A line is drawn across the surface of a coated polycarbonate plaque using a Sharpie marker (available from Sanford, Bellwood, Ill.). The samples are rated for appearance and for the ability to repel a black Sharpie marker.

| Ink Repellency Test Ratings | |
| --- | --- |
| Ranking | Description |
| 1 | Ink beaded into discrete hemispherical droplets |
| 2 | Ink beaded into discrete elongated droplets |
| 3 | Ink line narrowed and is discontinuous |
| 4 | Ink line is continuous and is not narrowed |

Ink Repellency Durability Test

A modified Oscillating Sand Method (ASTM F 735-94) is used to measure the durability of ink repellency of coated polycarbonate plaques. A coated polycarbonate plaque (i.e., test sample prepared as described above) is secured using vinyl tape and rubber bands onto an 87 mm inner diameter VWR 36318-860 jar (VWR Bristol, Conn.), containing 50 grams of unused 20-30 mesh Ottawa sand (VWR, Bristol, Conn.). The jar is placed in a VWR DS-500E shaker (VWR Bristol, Conn.) with the side containing the test sample at the bottom. The shaker is operated at an oscillating rate of 225 rpm for 10 minutes. At the end of ten minutes, the polycarbonate plaque is removed and a Sharpie permanent marker is used to draw a line across its surface that was in contact with the sand. The normalized (%) length of the portion of the 87 mm ink line that has not beaded up is measured and is reported as percent ink repellency loss. The data reported is the average of three independent tests.

Taber Haze Test

This test is run on polycarbonate plaques coated as described above. The test procedure is that of Procedure No CET-APRS-STP-0316, Revision 1.1, dated 24 Oct. 2005 by National Institute of Occupational Safety and Health. An average increase in haze less than 4% is desired.

Stain Cleaning Level Test

This test is run on polycarbonate plaques coated as described above. The test procedure is that of ASTM D 6578-00, Standard Practice for Determination of Graffiti Resistance. The standard has the following levels of cleanability after staining with paint and solvent based ink.

| Stain Cleaning Level | |
|---|---|
| Ranking | Cleanable with |
| 1 | Dry cotton cloth |
| 2 | 1% aqueous detergent solution |
| 3 | Citrus cleaner |
| 4 | Isopropanol alcohol |
| 5 | MEK |
| NC | Not Cleanable |
| R | Repellent |

Steel Wool Durability Test

The abrasion resistance of coated and cured polycarbonate plaques (prepared as described above) are tested cross-web to the coating direction by use of a mechanical device capable of oscillating a steel wool sheet adhered to a stylus across the film's surface. The stylus oscillated over a 90 mm wide sweep width at a rate of 315 mm/sec (3.5 wipes/sec) wherein a "wipe" is defined as a single travel of 90 mm. The stylus had a flat, cylindrical base geometry with a diameter of 3.2 cm. The stylus was designed to enable attachment of additional weights to increase the force exerted by the steel wool normal to the film's surface. The samples are tested at a 500 g load for 25 wipes. The #0000 steel wool sheets are "Magic Sand-Sanding Sheets" (Hut Products, Fulton, Mo.). The #0000 has a specified grit equivalency of 600-1200 grit sandpaper. The 3.2 cm steel wool discs are die cut from the sanding sheets and adhered to the 3.2 cm stylus base with 3M Brand Scotch Permanent Adhesive Transfer tape (3M, St. Paul, Minn.). The contact angles are measured on the wear track after the steel wool abrasion, and on an area of the plaque adjacent to the wear track that is not affected by the steel wool track (i.e., before steel wool testing). The contact angle measurements are made using the "method for Measuring Contact Angles" as described below. Unless otherwise noted, the data is reported based on an average of measurements done on three plaques. Three drops are placed on each plaque. The contact angle is measured on the right and left sides of each drop.

Method of Measuring Contact Angles

Polycarbonate substrates having hard-coat layers disposed thereon are pre-treated with a small quantity of isopropyl alcohol that is allowed to evaporate before the contact angle to the surface is measured. Measurements are made separately using as-received, reagent-grade n-hexadecane and de-ionized water filtered through a filtration system (Millipore Corporation Billerica, Mass.), on a video contact angle analyzer (Product number VCA2500XE from AST Products Billerica, Mass.). Drop volumes are 5 microliters (µL) for static measurements. The reported values are the averages of measurements on at least three drops of n-hexadecane and three drops water, unless otherwise noted. Measurements are taken on both the right and the left sides of the drops.

Solvent Resistance Test

Four chambers are each filled with a different solvent: ethanol, isopropanol, toluene and MEK. Plaques prepared as described above are placed in all four chambers for 60 seconds. Observations such as de-lamination, cracks, discoloration, and any other changes in the coating are recorded. Then, each plaque is placed in the solvent chambers for an additional 300 seconds. All observations are recorded.

Materials

Hexamethylene diisocyanate biuret (DESMODUR N100 or DESN100) (Bayer PolymersLLC of Pittsburgh, Pa.)

Hexamethylene diisocyanate isocyanurate (DESMODUR N3300 or DESN3300) (Bayer PolymersLLC of Pittsburgh, Pa.)

Isophonone diisocyanate (IPDI), 98% (MW=222.29) (Sigma-Aldrich, Milwaukee, Wis.)

HFPO—C(O)N(H)CH$_2$CH$_2$OH and HFPO—C(O)N(H)CH$_2$CH$_2$OC(O)CMe=CH$_2$ (HFPO-MAr, average molecular weight 1344) were prepared by a procedure similar to that described in U.S. Publication No. 2004-0077775, entitled "Fluorochemical Composition Comprising a Fluorinated Polymer and Treatment of a Fibrous Substrate Therewith."

SR444C Pentaerythritol Triacrylate (PET$_3$A) (Sartomer Company, Warrington, Pa.)

SHP 401 Poly(methyl methacrylate) Primer (Momentive Performance Materials, Inc., Waterford, N.Y.)

SHC 1200 Methylsilsesquioxane hard-coat solution (Momentive Performance Materials, Inc.)

N-methyl Aminopropyltrimethoxy silane (MAPTMS) (Union Carbide Chemicals and Plastics Co., Danbury, Conn.)

A-174 Methacryloyloxypropyl trimethoxysilane (Sigma-Aldrich, Milwaukee, Wis.)

Silquest A-1170 Bis(propyl-3-trimethoxysilane) amine (HN((CH$_2$)$_3$Si(OCH$_3$)$_3$)$_2$) (Momentive Performance Materials, Inc., Friendly, W. Va.)

Aminopropyltrimethoxy silane (APTMS), H$_2$N(CH$_2$)$_3$Si(OCH$_3$)$_3$, (Sigma-Aldrich)

Hydroxyethyl acrylate (HEA) (Sigma-Aldrich)

Dibutyltin dilaurate (DBTDL) (Sigma-Aldrich)

Silquest A-160 Mercaptopropyltrimethoxysilane (HS(CH$_2$)$_3$Si(OCH$_3$)$_3$) (Momentive Performance Materials)

Pentaerythritol triallyl ether in the form of a 70% technical grade solution (Sigma-Aldrich)

GE LEXAN101 Polycarbonate (Mount Vernon, Ind.) Plaques (molded by Minnesota Mold & Engineering, Vadnais Heights, Minn.).

DABCO 33LV 1,4-diazabicyclo[2.2.2]octane (Air Product and Chemicals, Inc., Allentown, Pa.)

VAZO 67 2,2'-azobis(2-methylbutyronitrile) (E.I. DuPont de Nemours & Co., Wilmington, Del.)

MeFBSE (C$_4$F$_9$SO$_2$N(CH$_3$)CH$_2$CH$_2$OH) was prepared by essentially following the procedure described in U.S. Pat. No. 6,664,354 (Savu et al.), Example 2, Part A.

Methyl Isobutyl Ketone (MIBK) (Burdick & Jackson, Muskegon, Mich.)

Tetrahydrofuran (THF) (EMD Chemicals, Gibbstown, N.J.)

Ethyl acetate (EtOAc) (EMD Chemicals, Gibbstown, N.J.)

Methyl ethyl ketone (MEK) (EMD Chemicals, Gibbstown, N.J.)

Thioethanol (Sigma-Aldrich, Milwaukee, Wis.)

NOVEC HFE-7100, C$_4$F$_9$OCH$_3$ (3M, St. Paul, Minn.)

Butylated hydroxytoluene (BHT) (Sigma-Aldrich)

The Preparations and Examples correspond to the fluorochemical silane urethane used. The Examples (coated plaques) may be prepared from different amounts of the same Preparation.

Where present, the ratios identified in the titles of Preparations 1-19 are based on moles, whereas the ratios identified in the titles of Preparations 20-23 are based on weight.

Preparation 1.

Preparation of Perfluoropolyether Urethane Silane DESN100/0.10 HFPO—C(O)N(H)CH$_2$CH$_2$OH/0.90 APTMS A 100 ml round bottom flask equipped with magnetic stirbar was charged with 6.25 g (0.0327 equivalents, 1.00 mole fraction) DESN100, 17.69 g tetrahydrofuran (THF), and 0.00079 g DBTDL (50 ppm based on the total solids to be charged, added from a 10% solids solution of DBTDL in methyl ethyl ketone), and placed in an oil bath at 55 degrees Centigrade under a nitrogen atmosphere. To the reaction was added 4.30 g (0.0033 eq, molecular weight 1314, 0.10 mole fraction) HFPO—C(O)N(H)CH$_2$CH$_2$OH via a dropping funnel over about 10 min. Two hours after the addition of the HFPO—C(O)N(H)CH$_2$CH$_2$OH was complete, 5.28 g (0.0295 eq, 0.90 mole fraction, 179.3 molecular weight) APTMS was added via a dropping funnel to the reaction over about 15 min. Two hours after the addition of the APTMS was complete, FTIR showed the absence of an isocyanate peak at 2265 cm-1. The reaction was adjusted to 50% solids by addition of 0.47 g THF, then diluted to 30% solids by addition of 21.11 g isopropanol.

Perfluoropolyether Urethane Silanes 2, 3 and 4 were made at 50% solids by the method used in the Preparation 1, using the relative number of mole fractions of ingredients listed in Table 1, and then diluted to 30% solids with isopropanol.

| Preparation Number | Mole fraction Des N100 | Mole fraction HFPOC(O)NHCH$_2$CH$_2$OH | |
|---|---|---|---|
| | | | Mole fraction H$_2$N(CH$_2$)$_3$Si(OCH$_3$)$_3$ |
| 2 | 1.0 | 0.15 | 0.85 |
| | | | Mole fraction HN((CH$_2$)$_3$Si(OCH$_3$)$_3$)$_2$ |
| 3 | 1.0 | 0.15 | 0.85 |
| | | | Mole fraction HS(CH$_2$)$_3$Si(OCH$_3$)$_3$ |
| 4 | 1.0 | 0.15 | 0.85 |

Preparation 5

30 g, 0.15 eq. isocyanate DESMODUR N3300A, 40.3 g, 0.03 mol HFPO—C(O)N(H)CH$_2$CH$_2$OH, 43.8 g solution, 31 g, 0.12 mol pentaerythritol triallyl ether, and 445 g MIBK were charged into 1 L flask. The mixture was heated to 8° C. while stirring and a solution was formed. The solution was purged with N$_2$ for 1 minute and three drops each of DBTDL and DABCO 33LV were added to it. The resulting solution was then heated to 110° C. for 15 hours. At the end of the 15 hours, the IR spectrum of a sample had no peaks corresponding to a NCO group. The solution was then allowed to cool to 70° C. and 70.7 g, 0.36 mol mercaptopropyltrimethoxysilane was then added. After the solution was purged with N$_2$ for 3 minutes and 0.7 g VAZO 67 was added to it, the solution was heated for 16 hours at 70° C. Following this period, there were no allylic groups remaining as determined from IR spectrum of a sample. The product fluorochemical urethane silane was a golden solution with 28% solids content.

Preparation 6

30 g, 0.15 eq isocyanate DESMODUR N3300A, 40.3 g, 0.03 mol HFPO—C(O)N(H)CH$_2$CH$_2$OH, 10.7 g, 0.03 mol MeFBSE, 33 g solution, 23 g, 0.09 mol pentaerythritol triallyl ether, and 445 g MIBK were charged into a 1 L flask. The mixture was heated to 80° C. while stirring and a solution was formed. The solution was purged with N$_2$ for 1 minute and three drops each of DBTDL and DABCO 33LV were added to it. The resulting solution was heated to 110° C. for 15 hours. At the end of the 15 hours, the IR spectrum of a sample had no peaks corresponding to a NCO group. The solution was then allowed to cool to 70° C. and the 53 g, 0.26 mol mercaptopropyltrimethoxysilane was added to it. After the resulting solution was purged with N$_2$ for 3 minutes and 0.7 g VAZO 67 was added to it, the solution was heated at 70° C. for 16 hours. Following this period, there were no allylic groups remaining as determined from IR spectrum of a sample. The product fluorochemical urethane silane was a golden solution with 25% solids content.

Preparation 7

28.6 g, 0.15 eq isocyanate DESMODUR N100, 40.3 g, 0.03 mol HFPO—C(O)N(H)CH$_2$CH$_2$OH, 43.8 g solution, 31 g, 0.12 mol pentaerythritol triallyl ether, and 445 g MIBK were charged into a 1 L flask. The mixture was heated to 80° C. while stirring and a solution was formed. The solution was purged with N$_2$ for 1 minute and three drops each of DBTDL and DABCO 33LV were added it. The resulting solution was heated to 110° C. for 15 hours. At the end of the 15 hours, the IR spectrum of a sample had no peaks corresponding to a NCO group. The solution was then allowed to cool to 70° C. and 70.7 g, 0.36 mol of mercaptopropyltrimethoxysilane was added to it. After the resulting solution was purged with N$_2$ for 3 minutes and 0.7 g VAZO 67 was added to it, the solution was heated at 70° C. for 16 hours. Following this period, there were no allylic groups remaining as determined from IR spectrum of a sample. The product fluorochemical urethane silane was a golden solution with 27.2% solids content.

Preparation 8

28.6 g, 0.15 eq isocyanate DESMODUR N100, 40.3 g, 0.03 mol HFPO—C(O)N(H)CH$_2$CH$_2$OH, 10.7 g, 0.03 mol MeFBSE, 33 g solution, 23 g, 0.09 mol pentaerythritol triallyl ether, and 445 g MIBK were added into a 1L flask. The mixture heated to 80° C. while stirring and a solution was formed. The solution was purged with N$_2$ for 1 minute and three drops each of DBTDL and DABCO 33LV were added to it. The resulting solution was heated to 110° C. for 15 hours. At the end of the 15 hours, the IR spectrum of a sample had no peaks corresponding to a NCO group. The solution was then allowed to cool to 70° C. and 53 g, 0.26 mol mercaptopropyltrimethoxysilane was added to it. After the resulting solution was purged with N$_2$ for 3 minutes and 0.7 g VAZO 67 was added to it, the solution was heated at 70° C. for 16 hours. Following this period, there were no allylic groups remaining as determined from IR spectrum of a sample. The product fluorochemical urethane silane was a golden solution with 25.6% solids content.

Preparation 9 a) Preparation of [DESN100/0.15 HFPOC(O)N(H)CH$_2$CH$_2$OH/0.90 HEA] Intermediate A 200 mL round bottom flask equipped with stirring bar was charged with 12.5 g (0.0654 eq, 1.0 mole fraction, 191.0 isocyanate equivalent weight) DESN100, 1.6 mg (50 ppm with respect to solids) DBTDL, 0.05 g BHT, and 32.24 g THF to form a mixture. The flask was placed in a 55° C. bath and 12.90 g (0.0098 eq, 0.15 mole fraction, 1314 molecular weight) HFPOC(O)N(H)CH$_2$CH$_2$OH was added to the mixture over 10 minutes via a pressure equalizing dropping funnel. Two hours after the addition was complete, 6.84 g (0.0589 eq, 0.90 mole fraction) hydroxyethyl acrylate was added and the mixture was allowed to react overnight. After reaction overnight, the IR spectrum of a sample had no peaks corresponding to a NCO group at 2265 cm$^{-1}$. The reaction product was diluted by addition of 5.48 g of THF to adjust its composition to 50% solids.

b) Preparation of Perfluoropolyether Urethane Silane 5 g (0.004565 moles of acrylate functionality) of intermediate prepared above in a) was charged in a 25 ml round bottom flask equipped with magnetic stirring bar. The flask was placed in an oil bath and the contents of the flask were placed under a nitrogen atmosphere. 1.56 g (0.004565 moles)

of bis(trimethoxysilylpropyl)amine was added into the flask dropwise at room temperature. The reaction mixture was stirred at room temperature for 15 minutes and then heated to 55° C. for 4 hours. The completion of reaction was determined by the disappearance of acrylate peaks in $^1$H NMR spectrum. The product was stored under nitrogen atmosphere in amber colored bottles in a refrigerator prior to coating.

Preparation 10 a) Preparation of [DESN100/0.30 HFPOC(O)N(H)CH$_2$CH$_2$OH/0.75 HEA] Intermediate A 200 mL round bottom flask equipped with stirring bar was charged with 12.5 g (0.0654 eq, 1.0 mole fraction) DESN100, 1.6 mg DBTDL, 0.05 g BHT, and 44.0 g THF. The flask was placed in a 55° C. bath and 25.80 g (0.0196 eq, 0.30 mole fraction, 1314 molecular weight) HFPOC(O)N(H)CH$_2$CH$_2$OH was added to the flask over 10 minutes via a pressure equalizing dropping funnel. Two hours after the addition was complete, 5.70 g (0.0491 eq, 0.75 mole fraction) hydroxyethyl acrylate was added and the mixture was allowed to react overnight. After reaction overnight, the IR spectrum of a sample had no peaks corresponding to a NCO group at 2265 cm$^{-1}$. The reaction product was diluted by addition of 11.44 g of THF to adjust its composition to 50% solids.

b) Preparation of Perfluoropolyether Urethane Silane 5 g (0.00278 moles of acrylate functionality) of the intermediate prepared above in a) was charged in a 25 ml round bottom flask equipped with magnetic stirring bar. The flask was placed in an oil bath and the content of the flask were place under nitrogen atmosphere. 0.9493 g (0.00278 moles) of bis(trimethoxysilylpropyl)amine was added into the flask dropwise at room temperature. The reaction mixture was stirred at room temperature for 15 minutes and heated to 55° C. for 4 hours. The completion of the reaction was determined by the disappearance of acrylate peaks in the $^1$H NMR spectrum. The product was stored under a nitrogen atmosphere in amber colored bottles in a refrigerator prior to coating.

Preparation 11 a) Preparation of [DESN100/0.50 HFPOC(O)N(H)CH$_2$CH$_2$OH/0.55 HEA] Intermediate A 200 mL round bottom flask equipped with stirring bar was charged with 12.5 g (0.0654 eq, 1.0 mole fraction) DESN100, 1.6 mg DBTDL, 0.05 g BHT, and 59.88 g THF. The flask was placed in a 55° C. bath and 43.0 g (0.0327 eq, 0.50 mole fraction, 1314 molecular weight) HFPOC(O)N(H)CH$_2$CH$_2$OH was added to the flask over 10 minutes via a pressure equalizing dropping funnel. Two hours after the addition was complete, 4.18 g (0.0360 eq, 0.55 mole fraction) hydroxyethyl acrylate was added and the mixture was allowed to react overnight. After reaction overnight, the IR spectrum of a sample had no peaks corresponding to a NCO group at 2265 cm$^{-1}$. The reaction product was diluted by addition of 29.62 of THF to adjust its composition to 50% solids.

b) Preparation of Perfluoropolyether Urethane Silane 5 g (0.0015 moles of acrylate functionality) of the intermediate prepared above in a) was charged to a 25 ml round bottom flask equipped with magnetic stirring bar. The flask was placed in an oil bath and the contents of the flask were placed under a nitrogen atmosphere. 0.5138 g (0.0015 moles) of bis(trimethoxysilylpropyl)amine was added into the flask drop wise at room temperature. The reaction mixture was stirred at room temperature for 15 minutes and heated to 55° C. for 4 hours. The completion of the reaction was determined by the disappearance of acrylate peaks in the $^1$H NMR spectrum. The product was stored under nitrogen atmosphere in amber colored bottles in a refrigerator prior to coating.

Preparation 12 a) Preparation of [DESN100/75% HEA/15% PET$_3$A/15% HFPOC(O)NHCH$_2$CH$_2$OH] Intermediate A 200 mL round bottom flask equipped with stirring bar was charged with 12.5 g (0.0654 eq, 1.0 mole fraction) DESN100, 1.6 mg DBTDL, 0.05 g BHT, and 35.24 g THF. The flask was placed in a 55° C. bath and 12.9 g (0.0098 eq, 0.15 mole fraction, 1314 molecular weight) HFPOC(O)N(H)CH$_2$CH$_2$OH was added to the flask over 10 minutes via a pressure equalizing dropping funnel. Two hours after the addition was complete, 4.13 g (0.0098 eq, 0.15 mole fraction) PET$_3$A was added to the mixture. Two hours after the addition was complete, 5.70 g (0.0491 eq, 0.75 mole fraction) hydroxyethyl acrylate was added and the mixture was allowed to react overnight. After reaction overnight, the IR spectrum of a sample had no peaks corresponding to a NCO group at 2265 cm$^{-1}$. The reaction product was diluted by addition of 5.48 g of THF to adjust its composition to 50% solids.

b) Preparation of Perfluoropolyether Urethane Silane 35.24 g (0.046* moles of acrylate functionality) of the intermediate prepared above in 12a) was charged to a 100 ml round bottom flask equipped with magnetic stirring bar. The flask was placed in an oil bath and the contents of the flask were placed under a nitrogen atmosphere. 15.77 g (1.417 eq, 0.046 mole fraction) of bis(trimethoxysilylpropyl)amine was added into the flask drop wise at room temperature. The reaction mixture was stirred at room temperature for 15 minutes and heated to 55° C. for 4 hours. The completion of the reaction was determined by the disappearance of acrylate peaks in the $^1$H NMR spectrum. The product was stored under a nitrogen atmosphere in amber colored bottles in a refrigerator prior to coating.

*The number of equivalents of bis(trimethoxysilylpropyl)amine used was determined by first assuming that PET$_3$A of 420.94 OH equivalent weight used was 70% Pentaerythritol Triacrylate (298/421.4) and 30% Pentaerythritol Tetraacrylate. Next, the number of acrylate moieties present per mole of OH equivalent was determined by calculating the following equation: [the sum for all components of (number of acrylate moieties present in component)(hydroxyl equivalent weight of the total species)(component's fraction of the total species)]/molecular weight of component. For example, Pentaerythritol Triacrylate's values in the equation are: [(3)*(420.94)*(0.7)/(298)]+[(4)*(420.94)*(0.3)/352]=4.40. Thus the number of equivalents of acrylate from the PET$_3$A and HEA in preparation 12a) was (0.0098*4.40)+(0.0491)=0.0922. Since half of the solution was used for preparation 12b), the number of moles of acrylate in the reaction is 0.046. Similar calculations were made for Preparations 13, 14b), and 15.

Preparation 13

Preparation of Perfluoropolyether Urethane Silane 35.24 g (0.046 moles of acrylate functionality) of intermediate prepared as described above in Preparation 12a) was charged to a 100 ml round bottom flask equipped with magnetic stirring bar. The flask was placed in an oil bath and the contents of the flask were placed under a nitrogen atmosphere. 8.92 g (0.046 eq*, 1.417 fraction) of MAPTMS was added into the flask dropwise at room temperature. The reaction mixture was stirred at room temperature for 15 minutes and heated to 55° C. for 4 hours. The completion of the reaction was determined by the disappearance of acrylate peaks in the $^1$H NMR spectrum. The product was stored under a nitrogen atmosphere in amber colored bottles in a refrigerator prior to coating.

Preparation 14 a) Preparation of [DESN100/60% HEA/30% PET3A/15% HFPOC(O)NHCH$_2$CH$_2$OH] Intermediate A 200 mL round bottom flask equipped with stirring bar was charged with 12.5 g (0.0654 eq, 1.0 mole fraction) DESN100, 1.6 mg DBTDL, 0.05 g BHT, and 35.24 g THF. The flask was placed in a 55° C. bath and 12.9 g (0.0098 eq, 0.15 mole fraction, 1314 molecular weight) HFPOC(O)N(H) CH$_2$CH$_2$OH was added to the flask over 10 minutes via a pressure equalizing dropping funnel. Two hours after the addition was complete, 8.26 (0.0196 eq, 0.30 mole fraction) PET$_3$A was added to the mixture. Two hours after the addition was complete, 4.56 g (0.0393 eq, 0.6 mole fraction) hydroxyethyl acrylate was added and the mixture was allowed to react overnight. After reaction overnight, the IR spectrum of a sample had no peaks corresponding to a NCO group at 2265 cm$^{-1}$. The reaction product was diluted by addition of 5.48 g of THF to adjust its composition to 50% solids.

b) Preparation of Perfluoropolyether Urethane Silane 38.23 g (0.063 moles of acrylate functionality) of the intermediate prepared above in a) was charged to a 100 ml round bottom flask equipped with magnetic stirring bar. The flask was placed in an oil bath and the contents of the flask were placed under a nitrogen atmosphere. 21.49 g (0.063 eq, 1.927 mole fraction) of bis(trimethoxysilylpropyl)amine was added into the flask drop wise at room temperature. The reaction mixture was stirred at room temperature for 15 minutes and heated to 55° C. for 4 hours. The completion of the reaction was determined by the disappearance of acrylate peaks in the $^1$H NMR spectrum. The product was stored under a nitrogen atmosphere in amber colored bottles in a refrigerator prior to coating.

Preparation 15

Preparation of Perfluoropolyether Urethane Silane 38.23 g (0.063 moles of acrylate functionality) of the intermediate prepared as described above in Preparation 14a) was charged to a 100 ml round bottom flask equipped with magnetic stirring bar. The flask was placed in an oil bath and the contents of the flask were placed under a nitrogen atmosphere. 12.16 g (0.63 eq, 1.927 mole fraction) of MAPTMS was added into the flask drop wise at room temperature. The reaction mixture was stirred at room temperature for 15 minutes and heated to 55° C. for 4 hours. The completion of the reaction was determined by the disappearance of acrylate peaks in the $^1$H NMR spectrum. The product was stored under a nitrogen atmosphere in amber colored bottles in a refrigerator prior to coating.

Synthesis of oligomeric silane (OSi-1) H(A-174)$_3$—SCH$_2$CH$_2$OH (average molecular weight=822):

A 200 mL bottle was charged with 14.90 g A-174 (MW=248.4, 60 mmol), 1.56 g HSCH$_2$CH$_2$OH (MW=78, 20 mmol), 38.4 g EtOAc and 0.3 g VAZO-67. After bubbling with nitrogen for 1 minute, the sealed bottle was heated in a 70° C. oil bath with magnetic stirring for 24 hours, which gave a clear solution at 30% solids. From FTIR analysis, no CH$_2$=CMeC(O)— signal was observed, indicating the completed oligomerization.

Synthesis of oligomeric silane (OSi-2) H(A-174)$_4$(ODA)$_{0.7}$-SCH$_2$CH$_2$OH (average molecular weight=1294):

In an 200 mL bottle, charged with 39.74 g A-174 (MW=248.4, 160 mmol), 8.70 g octadecyl acrylate (ODA) (MW=324, 26.8 mmol), 3.12 g HSCH$_2$CH$_2$OH (MW=78, 40 mmol), 103.3 g EtOAc and 10.g VAZO-67. After bubbling with nitrogen for 1 minute, the sealed bottle was heated in a 70° C. oil bath with magnetic stirring for 10 hours. Additional 0.70 g VAZO-67 was added and the oligomerization was continued for another 14 hours, which gave a clear solution in 33% solids. From FTIR analysis, no CH$_2$=CMeC(O)-signal was observed, indicating the completed oligomerization.

Preparation 16

Preparation of Perfluoropolyether Urethane Silane DESN100/0.33 HFPOC(O)N(H)CH$_2$CH$_2$OH/0.330Si-1/0.33 APTMS A 200 mL bottle was charged with 5.73 g DESN100 (EW=190, 30 mmol), 13.14 g HFPOC(O)N(H)CH$_2$CH$_2$OH (MW=1314, 10 mmol), 27.4 g of 30% OSi-1 (8.22 g solid, 10 mmol), 49.5 g EtOAc solvent and 5 drops of DBTDL catalyst. The sealed bottle was heated at 70° C. oil bath with magnetic stirring for 4 hours. Then, 2.21 g APTMS (10 mmol) was added at room temperature, and the mixture was reacted at room temperature for 0.5 hour, followed by reaction at 70° C. for another 4 hours. A clear solution in 30% solids was obtained. From FTIR analysis, no unreacted —NCO signal was observed, indicating the completed reaction.

Preparation 17

Perfluoropolyether Urethane Silane DESN3300/0.33 HFPOC(O)N(H)CH$_2$CH$_2$OH/0.33 OSi-1/0.33 APTMS Preparation 17 was prepared by a procedure similar to Preparation 16, with the exception that 5.76 g DESN3300 was used instead of DESN100.

Preparation 18

Perfluoropolyether Urethane Silane DESN100/0.33 HFPOC(O)N(H)CH$_2$CH$_2$OH/0.66 OSi-2

A 200 mL bottle was charged with 2.93 g DESN100 (EW=190, 15.34 meq), 6.71 g HFPOC(O)N(H)CH$_2$CH$_2$OH (MW=1314, 5.1 meq), 38.90 g of 33% solids OSi-2 (12.99 g solids, 10 meq OH), 22.5 g EtOAc solvent and 4 drops of DBTDL catalyst. The sealed bottle was heated at 70° C. oil bath with magnetic stirring for 8 hours. From FTIR analysis, no unreacted —NCO signal was observed, indicating complete reaction.

Preparation 19

Perfluoropolyether Urethane Silane: DESN100/0.23 HFPOC(O)N(H)CH$_2$CH$_2$OH/0.75 OSi-2

A 200 mL bottle was charged with 2.55 g DESN100 (EW=190, 13.35 meq NCO), 4.20 g HFPOC(O)N(H)CH$_2$CH$_2$OH (MW=1344, 3.12 meq), 38.90 g 33% solids OSi-2 (12.99 g solids, 10 meq OH), 20 g EtOAc solvent and 4 drops of DBTDL catalyst. The sealed bottle was reacted at 70° C. oil bath with magnetic stirring for 8 hours. From FTIR analysis, no unreacted —NCO signal was observed, indicating the completed reaction.

Preparation 20

Perfluoropolyether Acrylate Silane by weight 1.0 HFPOC(O)N(H)CH$_2$CH$_2$OC(O)CH(CH$_3$)=CH$_2$/9.0 A-174/0.2 A-160

A 100 mL bottle was charged with 1.0 g HFPOC(O)N(H)CH$_2$CH$_2$OC(O)CH(CH$_3$)=CH$_2$ (MW~1344, 0.744 mmol), 9.0 g A-174 (MW=248, 36.3 mmol), 0.2 g A-160 (MW=198, 1.02 mmol), 30 g MEK and 0.2 g VAZO-67. A stream of nitrogen was bubbled through the solution for 1 min, then the bottle was heated at 70° C. for 24 hours.

Preparation 21

Perfluoropolyether Acrylate Silane by weight 2.0 HFPOC(O)N(H)CH$_2$CH$_2$OC(O)CH(CH$_3$)=CH$_2$/8.0 A-174/0.2 A-160

A 100mL bottle was charged with 2.0 g HFPOC(O)N(H)CH$_2$CH$_2$OC(O)CH(CH$_3$)=CH$_2$ (MW~1344, 1.48 mmol), 8.0 g A-174 (MW=248, 32.2 mmol), 0.2 g A-160 (MW=198, 1.02 mmol), 30 g MEK and 0.2 g VAZO-67. A stream of nitrogen was bubbled through the solution for 1 min, then the bottle was heated at 70° C. for 24 hours.

Preparation 22

Perfluoropolyether Acrylate Silane by weight 4.0 HFPOC(O)N(H)CH$_2$CH$_2$OC(O)CH(CH$_3$)=CH$_2$/6.0 A-174/0.2 A-160

A 100 mL bottle was charged with 4.0 g HFPOC(O)N(H)CH$_2$CH$_2$OC(O)CH(CH$_3$)=CH$_2$ (MW~1344, 2.97 mmol), 6.0 g A-174 (MW=248, 24.2 mmol), 0.2 g A-160 (MW=198, 1.02 mmol), 30 g MEK and 0.2 g VAZO-67. A stream of nitrogen was bubbled through the solution for 1 min, then the bottle was heated at 70° C. for 24 hours.

Preparation 23

Perfluoropolyether Acrylate Silane by weight 6.0 HFPOC(O)N(H)CH$_2$CH$_2$OC(O)CH(CH$_3$)=CH$_2$/4.0 A-174/0.2 A-160

A 100 mL bottle was charged with 6.0 g HFPO-MAr (MW~1344, 4.46 mmol), 4.0 g A-174 (MW=248, 16.1 mmol), 0.2 g A-160 (MW=198, 1.02 mmol), 30 g MEK and 0.2 g VAZO-67. A stream of nitrogen was bubbled through the solution for 1 min, then the bottle was heated at 70° C. for 24 hours. A clear solution was obtained after reaction at 70° C., however, cloudy at room temperature, so 15 g HFE-401 was added to make a clear solution for formulation.

Example 1

Coated Plaques were Prepared According to the Following Procedure

Polycarbonate substrates (10 cm by 10 cm) were coated with hard-coat coating compositions using the dip coating process. To form the coatings, each polycarbonate plaque was first immersed into a solution of SHP 401 primer at a rate of 90 cm per minute. Once the entire substrate was immersed in the primer, the substrate was removed from the primer at a rate of 90 cm per minute and was allowed to air dry at room temperature for 10 minutes. The dried substrate was then immersed into a solution of SHC-1200 or a solution of SHC-1200 containing 0.3 weight percent of a fluorinated urethane silane (unless otherwise noted), at a rate of 90 cm per minute and withdrawn at a rate of 19 cm per minute, air dried at room temperature for 20 minutes and finally heated in an oven for 30 minutes at 130° C.

The Example numbers correspond to the Preparation numbers in the preceding section. For each Example, a small quantity of the corresponding Preparation was blended into a quantity of SHC-1200 such that the solids weight of the Preparation was 0.3% of the solids weight of the SHC-1200. To illustrate: Preparation 1 is 30% solids, so 1 gram of Preparation 1 contains 0.3 gram solids. SHC-1200 is 19% solids; so 526 grams of SHC-1200 contains 100 grams of solids. Mixing 1 gram of Preparation 1 with 526 grams of SHC-1200 yields a solids weight percent of 0.3%. This mixture was used to coat the plaques of Example 1.

Three Examples were prepared with Preparation 2 and these are identified as Examples 2a, 2b, and 2c. For Example 2a, the solids weight percent of Preparation 2 in SHC-1200 was 0.2%; for Example 2b the solids weight percent is 0.3%; and for Example 2c the solids weight percent is 0.4%.

A Comparative Example was also prepared by coating a plaque with unmodified SHC-1200.

Table 1 below summarizes the results of Taber Haze Test, Ink Repellency Test and Ink Repellency Durability Test for the Comparative Example and Examples made from Preparations 1-15.

TABLE 1

| Example | Preparation | Level of fluorinated urethane silane if different than 0.3% | Taber Haze Test | Ink Repellency Test | Ink Repellency Durability Test, % |
|---|---|---|---|---|---|
| Comparative Example 1 | SHC-1200 | 0% | 3.57 | 4 | 100 |
| 1 | 1 | | 2.99 | 1 | 33 |
| 2a | 2 | 0.2% | 2.93 | 1 | 17 |
| 2b | 2 | | 2.78 | 1 | 50 |
| 2c | 2 | 0.4% | 2.76 | 1 | 17 |
| 3 | 3 | | 2.15 | 1 | 8 |
| 4 | 4 | | 2.99 | 1 | 43 |
| 5 | 5 | | 3.59 | 2.5 | 100 |
| 6 | 6 | | 3.88 | 1 | 57 |
| 7 | 7 | | 3.24 | 1 | 72 |
| 8 | 8 | | 3.50 | 1 | 87 |
| 9 | 9 | | 2.22 | 1 | 7 |
| 10 | 10 | | 3.05 | 2 | 70 |
| 11 | 11 | | 3.47 | 1 | 97 |
| 12 | 12 | | 3.06 | 1 | 94 |
| 13 | 13 | | 2.49 | 1 | 94 |
| 14 | 14 | | 2.97 | 1 | 100 |
| 15 | 15 | | 3.12 | 1 | 100 |

Table 2 below summarizes the results of Steel Wool Test for the Comparative Example 1 and Examples made from Preparations 1-15.

TABLE 2

| Example | Level of fluorinated urethane silane if different than 0.3% | Before Steel Wool Test | | After Steel Wool Test | |
|---|---|---|---|---|---|
| | | Water Contact Angle degree | Standard Deviation | Water Contact Angle degree | Standard Deviation |
| Comparative Example 1 | 0% | 94.1 | 1.3 | 87.6 | 1.9 |
| 1 | | 105.8 | 1.1 | 104.5 | 0.6 |
| 2a | 0.2% | 106.6 | 0.8 | 106.1 | 1.7 |
| 2b | | 105.3 | 1.1 | 104.9 | 0.8 |
| 2c | 0.4% | 107.2 | 0.6 | 106.2 | 1.2 |
| 3 | | 106.0 | 0.6 | 105.1 | 1.1 |
| 4 | | 107.3 | 0.7 | 106.4 | 0.8 |
| 5 | | 99.5 | 0.5 | 97 | 1.3 |
| 6 | | 106.5 | 0.6 | 104.4 | 1.5 |
| 7 | | 101.1 | 1.2 | 99.5 | 1.0 |
| 8 | | 102.5 | 0.8 | 100.9 | 1.1 |
| 9 | | 107.1 | 0.9 | 105.5 | 1.7 |
| 10 | | 104.9 | 0.7 | 103 | 1.4 |
| 11 | | 96.5 | 1.1 | 93.7 | 2.3 |
| 12 | | 100.3 | 0.5 | 98.3 | 0.7 |
| 13 | | 100.4 | 0.5 | 97.7 | 1 |
| 14 | | 97.4 | 0.5 | 93 | 0.9 |
| 15 | | 97.7 | 0.9 | 92.5 | 1.4 |

Table 3 below summarizes the hexadecane contact angles found for selected Examples, before Steel Wool Testing.

TABLE 3

| Example | Level of fluorinated urethane silane if different than 0.3% | Hexadecane Contact Angle degree | Standard Deviation |
|---|---|---|---|
| Comparative Example 1 | 0% | 36.9 | 1.0 |
| 1 | | 67.5 | 2.5 |
| 2a | 0.2% | 67.6 | 1.8 |
| 2b | | 68.6 | 3.5 |
| 2c | 0.4% | 67.7 | 1.6 |

Table 4 below summarizes the results of Solvent Test for the Comparative Example 1 and selected Examples made from Preparations 1-1.

TABLE 4

| Example | Level of fluorinated urethane silane if different than 0.3% | Solvent | After 60 seconds | After 300 seconds |
|---|---|---|---|---|
| Comparative Example 1 | 0% | Ethanol | No effect | No effect |
| Comparative Example 1 | 0% | Isopropanol | No effect | No effect |
| Comparative Example 1 | 0% | Toluene | No effect | No effect |
| Comparative Example 1 | 0% | MEK | No effect | Few tiny cracks by edges |
| 1 | | Ethanol | No effect | No effect |
| 1 | | Isopropanol | No effect | No effect |
| 1 | | Toluene | No effect | Some tiny cracks, mostly by edges |
| 1 | | MEK | Tiny cracks | White spots and cracks all over coating |
| 2a | 0.2% | Ethanol | No effect | No effect |
| 2a | 0.2% | Isopropanol | No effect | No effect |
| 2a | 0.2% | Toluene | No effect | Few tiny cracks |
| 2a | 0.2% | MEK | No effect | Tiny cracks in coating, mostly by edges |
| 2b | | Ethanol | No effect | No effect |
| 2b | | Isopropanol | No effect | No effect |
| 2b | | Toluene | No effect | Only a couple small cracks in coating |
| 2b | | MEK | No effect | Some tiny cracks, mostly by edges |
| 2c | 0.4% | Ethanol | No effect | No effect |
| 2c | 0.4% | Isopropanol | No effect | No effect |
| 2c | 0.4% | Toluene | No effect | Only a couple small cracks in coating |
| 2c | 0.4% | MEK | Few white spots | White spots, tiny cracks, de-lamination by edges |
| 4 | | Ethanol | No effect | No effect |
| 4 | | Isopropanol | No effect | No effect |
| 4 | | Toluene | Few tiny cracks | Larger cracks in coating |
| 4 | | MEK | Tiny cracks and white spots | Larger cracks and white spots all over coating |
| 5 | | Ethanol | No effect | No effect |
| 5 | | Isopropanol | No effect | No effect |
| 5 | | Toluene | No effect | Few small white spots but no cracks |
| 5 | | MEK | Some white spots | White spots and cracks all over coating, de-lamination |
| 6 | | Ethanol | No effect | No effect |
| 6 | | Isopropanol | No effect | No effect |
| 6 | | Toluene | No effect | Cracks and some de-lamination by edges |
| 6 | | MEK | Few tiny cracks | White spots and cracks all over coating, de-lamination |
| 7 | | Ethanol | No effect | No effect |
| 7 | | Isopropanol | No effect | No effect |
| 7 | | Toluene | No effect | Cracks and some de-lamination by edges |
| 7 | | MEK | No effect | Cracks and some de-lamination by edges |
| 8 | | Ethanol | No effect | No effect |
| 8 | | Isopropanol | No effect | No effect |

TABLE 4-continued

| Example | Level of fluorinated urethane silane if different than 0.3% | Solvent | After 60 seconds | After 300 seconds |
|---|---|---|---|---|
| 8 | | Toluene | No effect | Few tiny cracks |
| 8 | | MEK | No effect | Cracks and some white spots, de-lamination by edges |
| 9 | | Ethanol | No effect | No effect |
| 9 | | Isopropanol | No effect | No effect |
| 9 | | Toluene | No effect | Few tiny cracks |
| 9 | | MEK | No effect | Long and thin cracks all over coating |
| 10 | | Ethanol | No effect | No effect |
| 10 | | Isopropanol | No effect | No effect |
| 10 | | Toluene | No effect | Few tiny cracks |
| 10 | | MEK | No effect | Few tiny cracks, de-lamination by edges |
| 11 | | Ethanol | No effect | No effect |
| 11 | | Isopropanol | No effect | No effect |
| 11 | | Toluene | No effect | Few tiny cracks |
| 11 | | MEK | Tiny cracks all over coating | Tiny cracks and white spots all over, de-lamination by edges |

Table 5 below summarizes the results of Stain Cleaning Level Test for the Comparative Example 1 and Selected Examples made from Preparations 1-15.

TABLE 5

| Example | Level of fluorinated urethane silane if different than 0.3% | Paint Stain Cleaning Level | Solvent based Ink Cleaning level |
|---|---|---|---|
| Comparative Example 1 | 0% | 3 | 3R |
| 2b | | 1R | 1R |
| 3 | | 1R | 1R |
| 9 | | 1R | 1R |
| 12 | | 3R | 1R |
| 13 | | 3R | 1R |
| 14 | | 3 | 1R |
| 15 | | 4 | 1R |

Table 6 below summarizes the results of Steel Wool Test for the Examples made from Preparations 16-19. All examples had Ink Repellency Test ratings of 1 before and after Steel Wool Testing. Contact angle values before Steel Wool Testing were from an average of two readings. Contact angle values after Steel Wool Testing were from a single reading.

TABLE 6

| | Before Steel Wool Test | | After Steel Wool Test | |
|---|---|---|---|---|
| Example | Water Contact Angle | Hexadecane Contact Angle | Water Contact Angle | Hexadecane Contact Angle |
| 16 | 106 | 71 | 104 | 69 |
| 17 | 109 | 70 | 105 | 70 |
| 18 | 106 | 67 | 90 | 63 |
| 19 | 104 | 61 | 101 | 66 |

Table 7 below summarizes the results of Steel Wool Test for the Examples made from Preparations 20-23. All examples had Ink Repellency Test ratings of 1 before and after Steel Wool Testing. Contact angle values before Steel Wool Testing were from an average of two readings. Contact angle values after Steel Wool Testing were from a single reading.

TABLE 7

| | Before Steel Wool Test | | After Steel Wool Test | |
|---|---|---|---|---|
| Example | Water Contact Angle | Hexadecane Contact Angle | Water Contact Angle | Hexadecane Contact Angle |
| 20 | 102 | 55 | 101 | 54 |
| 21 | 102 | 56 | 104 | 55 |
| 22 | 103 | 66 | 109 | 68 |
| 23 | 108 | 64 | 105 | 63 |

Other embodiments are within the claims. All references referred to herein are incorporated by reference.

What is claimed is:

1. A respirator, welding helmet or face shield comprising:
   a lens; and
   a hard-coat disposed on the lens, the hard-coat comprising the reaction product of
   a) an additive comprising at least one of
      i) perfluoropolyether urethane comprising hydrolysable silane groups, and
      ii) an acrylate polymer comprising at least one perfluoropolyether moiety and at least one hydrolysable silane group, and
   b) at least 50% by weight silsesquioxane-based hard-coat composition.

2. The respirator, welding helmet or face shield of claim 1 further comprising a primer coating disposed between the lens and the hard-coat.

3. The respirator, welding helmet or face shield of claim 1, wherein the reaction product comprises from about 0.01% by weight to about 10% by weight of the additive.

4. The respirator, welding helmet or face shield of claim 1, wherein the reaction product comprises from about 0.1% by weight to about 1% by weight of the additive.

5. The respirator, welding helmet, or face shield of claim 1, wherein the lens comprises at least one of polycarbonate, polymethylmethacrylate, polyethylene, polypropylene, polyethylene terephthalate, polystyrene, and combinations thereof.

6. The respirator, welding helmet, or face shield of claim 1, wherein the lens comprises glass.

7. The respirator, welding helmet or face shield of claim 1, wherein the hard-coat comprises the reaction product of the perfluoropolyether urethane and silsesquioxane-based hard-coat composition, the perfluoropolyether urethane being of the formula

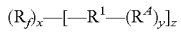

wherein
$R_f$ is a fluorine-containing group comprising a perfluorooxyalkyl group or a perfluorooxyalkylene group,
$R^1$ is the residue of a polyisocyanate having a valence of x+y,
$R^A$ is of the formula:

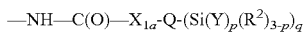

wherein
Q is a connecting group of valency at least 2,
$X_{1a}$ is O, S, or NR, wherein R is H, aryl, a lower alkyl of 1 to 4 carbon atoms, or $Q\text{-}(Si(Y)_p(R^2)_{3-p})_q$,
Y is a hydrolysable group,
$R^2$ is a monovalent alkyl or aryl group,
p is 1, 2 or 3, and
q is 1 to 6,
x and y are each independently at least 1, and
z is at least 1.

8. The respirator, welding helmet or face shield of claim 1, wherein the hard-coat comprises the reaction product of the perfluoropolyether urethane and the silsesquioxane-based hard-coat composition, the perfluoropolyether urethane being of the formula

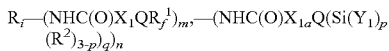

wherein
$R_i$ is a residue of a multi-isocyanate,
$X_1$ is O, S, or NR, wherein R is H, aryl, or a lower alkyl of 1 to 4 carbon atoms,
$X_{1a}$ is O, S, or NR, wherein R is H, aryl, a lower alkyl of 1 to 4 carbon atoms, or $Q\text{-}(Si(Y)_p(R^2)_{3-p})_q$,
$R_f^1$ is a monovalent perfluoropolyether moiety composed of groups comprising the formula $F(R_{fc}O)_w C_d F_{2d}$—,
wherein
each $R_{fc}$ independently represents a fluorinated alkylene group having from 1 to 6 carbon atoms,
each w independently represents an integer of at least 2, and
d is an integer from 1 to 6,
Q is independently a connecting group of valency at least 2,
$Y_1$ is a hydrolysable group selected from the group consisting of —$OR_2$ and —$OC(O)R_2$, wherein $R_2$ is a lower alkyl of 1 to 4 carbon atoms,
$R^2$ is a monovalent alkyl or aryl group,
m is at least 1,
n is at least 1,
p is 1, 2 or 3,
q is from to 6,
m+n is from 2 to 10, and
each unit referred to by the subscripts m and n is attached to an $R^1$ unit.

9. The respirator, welding helmet or face shield of claim 7, wherein Q comprises a straight chain connecting group, a branched chain connecting group, a cycle-containing connecting group, a covalent bond, an alkylene, an arylene, an aralkylene, an alkarylene, a heteroatom comprising O, N, or S, a heteroatom-containing functional group comprising carbonyl or sulfonyl, or a combination thereof.

10. The respirator, welding helmet or face shield of claim 7, wherein the perfluoropolyether urethane comprises at least one of

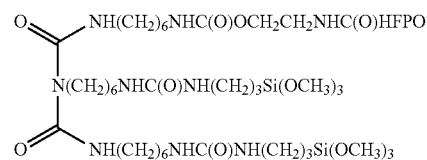

and

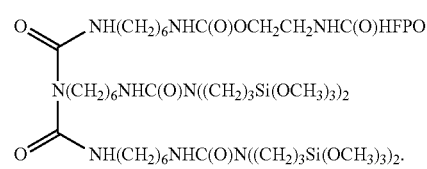

11. The respirator, welding helmet or face shield of claim 1, wherein the hard-coat comprises the reaction product of the perfluoropolyether urethane and the silsesquioxane-based hard-coat composition, the perfluoropolyether urethane comprising a compound of the formula

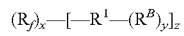

wherein
$R_f$ is a fluorine-containing group comprising a perfluorooxyalkyl group or a perfluorooxyalkylene group,
$R^1$ is the residue of a polyisocyanate having a valency of x+y,
$R^B$ is of the formula

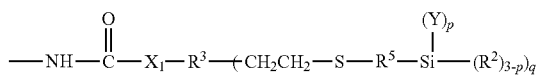

wherein
$X_1$ is O, S, or NR, wherein R is H, aryl, or a lower alkyl of 1 to 4 carbon
$R^3$ is a polyvalent group comprising alkylene, arylene, or a combination thereof, the alkylene group optionally comprising at least one catenary oxygen atom;
$R^5$ is a divalent alkylene group, the alkylene group optionally comprising at least one catenary oxygen atom;
Y is a hydrolysable group,
$R^2$ is a monovalent alkyl or aryl group,
p is 1, 2 or 3, and
q is 1 to 6,
x and y are each independently at least 1, and
z is at least 1.

12. The respirator, welding helmet or face shield of claim 11, wherein the perfluoropolyether urethane comprises

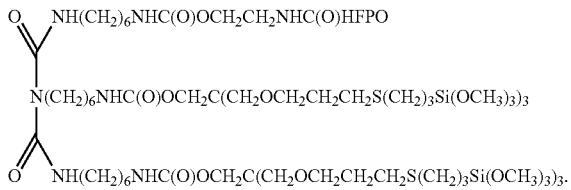

13. The respirator, welding helmet or face shield of claim 1, wherein the hard-coat comprises the reaction product of the perfluoropolyether urethane and the silsesquioxane-based hard-coat composition, the perfluoropolyether urethane comprising a compound of the formula $$(R_f)_x\text{---}[\text{---}R^1(R^C)_y]_z$$

wherein
- $R_f$ is a fluorine-containing group comprising a perfluorooxyalkyl group or a perfluorooxyalkylene group,
- $R^1$ is the residue of a polyisocyanate having a valency of x+y,
- $R^c$ is a silane-containing moiety derived from the Michael reaction between a nucleophilic acryloyl compound and an aminosilane,
- x and y are each independently at least 1, and
- z is at least 1.

14. The respirator, welding helmet or face shield of claim 13, wherein $R^c$ is derived by Michael addition of an aminosilane to an acryloyl group and is of the following formula $$\text{---}(NHC(O)X_2QX_1(C(O)CH_2CH_2\text{---}NR^4R^3Si(Y)_p(R^2)_{3-p})_q)_n$$

wherein
- $R^4$ is $R^3Si(Y)_p(R^2)_{3-p}$ or $R^2$,
- Q is a connecting group of valency at least 2,
- $X_1$ is O, S, or NR, wherein R is H, aryl, or a lower alkyl of 1 to 4 carbon atoms,
- $X_2$ is —O— or —S—,
- $R^3$ is a polyvalent group comprising alkylene, arylene or a combination thereof, optionally comprising at least one catenary oxygen atom;
- Y is a hydrolysable group,
- $R^2$ is a monovalent alkyl or aryl group,
- p is 1, 2 or 3,
- q is from 1 to 6, and
- n is at least 1.

15. The respirator, welding helmet or face shield of claim 13, wherein the perfluoropolyether urethane comprises

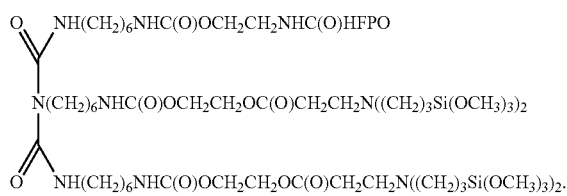

16. The respirator, welding helmet or face shield of claim 1, wherein the hard-coat comprises the reaction product of the acrylate polymer and the silsesquioxane-based hard-coat composition, the acrylate polymer being represented by the general formula $$X\text{-}M^f_iM^h_jM^a_k\text{-}G$$

wherein
- X represents the residue of an initiator or hydrogen,
- $M^f$ represents units derived from fluorinated monomers,
- $M^h$ represents units derived from non-fluorinated monomers,
- $M^a$ represents units having a silyl group represented by the formula $$Si(Y_1)_p(R^2)_{3-p},$$

wherein
- $Y_1$ is a hydrolysable group selected from the group consisting of —$OR_2$ and —$OC(O)R_2$, wherein $R_2$ is a lower alkyl of 1 to 4 carbon atoms, O $R^2$ is a monovalent alkyl or aryl group, and
- p is 1, 2 or 3,
- G is a monovalent organic group that includes the residue of a chain transfer agent,
- i represents a value of 1 to 100,
- j represents a value of 0 to 100,
- k represents a value of 0 to 100, and
- i+j+k is at least 2, with the proviso that at least one of the following conditions is fulfilled,
  - a. G is a monovalent organic group that contains a silyl group of the formula $$Si(Y_1)P(R^2)_{3-p}$$

wherein
- $Y_1$ is a hydrolysable group selected from the group consisting of —$OR_2$ and —$OC(O)R_2$, wherein $R_2$ is a lower alkyl of 1 to 4 carbon atoms,
- $R^2$ is a monovalent alkyl or aryl group, and
- p is 1, 2 or 3, and
  - b. k is at least 1.

17. The respirator, welding helmet or face shield of claim 1, wherein the hard-coat exhibits a static water contact angle of at least 95 degrees.

18. The respirator, welding helmet or face shield of claim 1, wherein the hard-coat exhibits a static water contact angle of at least 100 degrees.

19. The respirator, welding helmet or face shield of claim 1, wherein the hard-coat exhibits a static hexadecane contact angle of at least 50 degrees.

20. The respirator, welding helmet or face shield of claim 7, wherein $R^A$ is derived from a structure of the formula $$X\text{-}M^h_{j1}M^a_{k1}\text{-}S\text{-}Q^1\text{-}OH,$$

wherein
- X represents the residue of an initiator or hydrogen,
- $M^h$ represents units derived from non-fluorinated monomers,
- $M^a$ represents units having a silyl group represented by the formula $$Si(Y_1)_p(R^2)_{3-p},$$

wherein
- $Y_1$ is a hydrolysable group selected from the group consisting of —$OR_2$ and —$OC(O)R_2$, wherein $R_2$ is a lower alkyl of 1 to 4 carbon atoms,
- $R^2$ is a monovalent alkyl or aryl group, and
- p is 1, 2 or 3,
- $Q^1$ is a divalent organic linking group
- j1 is 0 to 20, and
- k1 is 2 to 20.

21. The respirator, welding helmet or face shield of claim 1, wherein perfluoropolyether urethane with reactive silane acrylate oligomer has the formula $$R_i\text{—}(NHC(O)X_1QR_f^1)_m\text{—}(NHC(O)\text{—}(O\text{-}Q^1\text{-}S\text{-}M^h{}_{j1}M^a{}_{k1}X)_n,$$

wherein
- $R_i$ is a residue of a multi-isocyanate,
- m is at least 1,
- n is at least 1,
- $X_i$ is O, S, or NR, wherein R is H, aryl, or a lower alkyl of 1 to 4 carbon atoms,
- $R_f^1$ is a monovalent perfluoropolyether moiety composed of groups comprising the formula $F(R_{fc}O)_wC_dF_{2d}\text{—}$,
  wherein
  - each $R_{fc}$ independently represents a fluorinated alkylene group having from 1 to 6 carbon atoms,
  - each w independently represents an integer of at least 2, and
  - d is an integer from 1 to 6,
- Q is independently a connecting group of valency at least 2,
- X represents the residue of an initiator or hydrogen,
- $M^h$ represents units derived from non-fluorinated monomers,
- $M^a$ represents units having a silyl group represented by the formula $$Si(Y_1)_p(R^2)_{3-p},$$

wherein
  - $Y_1$ is a hydrolysable group selected from the group consisting of $\text{—}OR_2$ and $\text{—}OC(O)R_2$, wherein $R_2$ is a lower alkyl of 1 to 4 carbon atoms,
  - $R^2$ is a monovalent alkyl or aryl group, and
  - p is 1, 2 or 3,
- $Q^1$ is a divalent organic linking group
- j1 is 0 to 20, and
- k1 is 2 to 20.

* * * * *

UNITED STATES PATENT AND TRADEMARK OFFICE
CERTIFICATE OF CORRECTION

PATENT NO. : 8,015,970 B2
APPLICATION NO. : 11/828566
DATED : September 13, 2011
INVENTOR(S) : Thomas P. Klun et al.

It is certified that error appears in the above-identified patent and that said Letters Patent is hereby corrected as shown below:

Column 2
Line 27, delete "acylic," and insert -- acyclic, --, therefor.
Line 58, delete "$CF_2O)U$" and insert -- $CF_2O)_u$ --, therefor.

Column 3
Line 28, delete "$CH_3$—O—" and insert -- $CH_3O$ --, therefor.
Line 56, delete "$CF_2O)_n$" and insert -- $CF_2O)_s$ --, therefor.
Line 61, delete "$[CF_2—CF_2—O]$" and insert -- $[CF_2—CF_2—O]_r$ --, therefor.

Column 4
Line 3, delete ""Pefluoropolyether" and insert -- "Perfluoropolyether --, therefor.

Column 6
Line 18, after "EP" delete "U.S. Pat No.".
Line 65, delete "$R^1$" and insert -- $R^A$ --, therefor.

Column 7
Line 3, delete "$X^{1a}$" and insert -- $X_{1a}$ --, therefor.
Line 13, delete "$R^1$—$(NHC(O)X_1QR_f^1)m$," and insert -- $R_i$— $(NHC(O)X_1QR_f^1)m$, --, therefor.
Line 41, delete "$R^1$ unit." and insert -- $R_i$ unit. --, therefor.

Column 8
Line 10, delete "$X-M^h_{j1}M^a_{k1}S-Q^1-OH(OSi)$," and insert -- $X-Mhj1Mak1-S-Q^1-OH(OSi)$, --, therefor.

Column 9
Line 36, delete "$C(0)NHCH_2$" and insert -- $C(O)NHCH_2$ --, therefor.

Signed and Sealed this
Third Day of January, 2012

David J. Kappos
*Director of the United States Patent and Trademark Office*

CERTIFICATE OF CORRECTION (continued)
U.S. Pat. No. 8,015,970 B2

Column 12
Line 50, delete "$(R_f)_x$—[—R— $(R^C)_y]_z$" and insert -- $(R_f)_x$—[—$R^1$—$(R^C)_y]_z$ --, therefor.
Line 65, delete "$R^4$" and insert -- $R_4$ --, therefor.

Column 15
Line 40, delete "$HX_2\text{-}R^3\text{-}[X_1\text{-}C(O)CH_2CH_2NR^4\text{-}R^3\text{-}Si(Y)_p(R^2)_{3-p}]_q$" and insert
-- $HX_2\text{-}R^3\text{-}[X_1\text{-}C(O)CH_2CH_2NR_4\text{-}R^3\text{-}Si(Y)_p(R^2)_{3-p}]_q$ --, therefor.

Column 16
Line 4, after "in" delete "which is".
Line 24, delete "$(R^1)$" and insert -- $(R_i)$ --, therefor.
Line 49, delete "(Pittsburgh, Pa.)," and insert -- (Pittsburgh, Pa.)), --, therefor.

Column 17
Line 26, delete "(IM)" and insert -- (1M) --, therefor.
Line 31, delete "(IM)" and insert -- (1M) --, therefor.
Line 45, delete "$W\text{-}R_f^3\text{-}O\text{-}R_f^4\text{-}(R_f^5)_{q1}$" and insert -- $W\text{-}R_f^3\text{-}O\text{-}R_f^4\text{-}(R_f^5)_{q1}\text{-}$ --, therefor.
Line 45, delete "(10)" and insert -- (1O) --, therefor.
Line 50, delete "$R_f^3$" and insert -- $R_f^4$ --, therefor.
Line 55, delete "Formula (10)" and insert -- Formula (1O) --, therefor.

Column 18
Line 6, delete "Formula (10)" and insert -- Formula (1O) --, therefor.

Column 19
Line 22, delete "$Si(Y_1P(R^2)_{3-p},$" and insert -- $Si(Y_1)_P(R^2)_{3-p}$, --, therefor.
Line 32, delete "$\text{-}SQ^1T^2C(O)NHQ^5Si(Y_1)(Y^2)(Y^3)$" and insert
-- $\text{-}SQ^1T^2C(O)NHQ^5Si(Y^1)(Y^2)(Y^3)\text{-}$ --, therefor.
Line 37, delete "T2" and insert -- $T^2$ --, therefor.
Line 39, delete "$Y_3$" and insert -- $Y^3$ --, therefor.
Line 41, delete "$Y_3$" and insert -- $Y^3$ --, therefor.

Column 20
Line 2, delete "$R^1$" and insert -- $R^h$ --, therefor.

Column 22
Line 16, delete "$A\text{-}Q^5Si(Y^1)(Y^2)(Y^3)$" and insert -- $A\text{-}Q^5\text{-}Si(Y^1)(Y^2)(Y^3)$ --, therefor.
Line 25, delete "$Y_3$" and insert -- $Y^3$ --, therefor.

Column 23
Lines 41-42, delete "silsequioxane-based" and insert -- silsesquioxane-based --, therefor.
Line 57, delete "tetralkoxysilanes" and insert -- tetraalkoxysilanes --, therefor.
Line 61, delete "silsequioxane-based" and insert -- silsesquioxane-based --, therefor.

CERTIFICATE OF CORRECTION (continued)
U.S. Pat. No. 8,015,970 B2

Column 28
Line 4, delete "Isophonone" and insert -- Isophorone --, therefor.

Column 29
Line 38, delete "DESMODURN3300A," and insert -- DESMODUR N3300A, --, therefor.
Line 41, delete "8°C." and insert -- 80°C. --, therefor.

Column 30
Line 29, delete "IL flask." and insert -- 1L flask. --, therefor.

Column 34
Line 5, delete "HFPOC(O)N(H)CH$_2$CH$_2$OH/0.330Si-1/" and insert
-- HFPOC(O)N(H)CH$_2$CH$_2$OH/0.33OSi-1/ --, therefor.

Column 35
Line 30, delete "Procedure" and insert -- Procedure: --, therefor.

Column 38
Line 12, delete "1-1." and insert -- 1-11. --, therefor.

Column 41
Line 62, in Claim 8, after "from" insert -- 1 --.
Line 65, in Claim 8, delete "$R^1$ unit." and insert -- $R_i$ unit. --, therefor.

Column 43
Line 20, in Claim 13, delete "$(R_f)_x—[—R^1(R^C)_y]_z$" and insert -- $(R_f)_x—[—R^1—(R^C)_y]_z$ --, therefor.
Line 36, in Claim 14, delete "—$NR^4R^3Si(Y)_p$," and insert -- —$NR_4R^3Si(Y)_p$ --, therefor.
Line 39, in Claim 14, delete "$R^4$" and insert -- $R_4$ --, therefor.

Column 44
Line 18, in Claim 16, after "atoms," delete "O".
Line 30, in Claim 16, delete "$Si(Y_1)P(R^2)_{3-p}$," and insert -- $Si(Y_1)_p(R^2)_{3-p}$, --, therefor.

Column 45
Line 4, in Claim 21, delete "-(NHC(O)-O-$Q^1$-S-$M^h_{j1}M^a_{k1}X)_n$," and insert
-- -(NHC(O)O-$Q^1$-S-$M^h_{j1}M^a_{k1}X)_n$, --, therefor.
Line 10, in Claim 21, delete "$X_i$" and insert -- $X_1$ --, therefor.